US008626266B1

(12) United States Patent
Frank et al.

(10) Patent No.: US 8,626,266 B1
(45) Date of Patent: Jan. 7, 2014

(54) ECG TRIGGERED HEART AND ARTERIAL MAGNETIC RESONANCE IMAGING

(75) Inventors: Thomas H. Frank, Crofton, MD (US); Otis R. Blaumanis, Sparks, MD (US); Joseph A. La Rosa, Baltimore, MD (US); Yvette M. Word, Pasadena, MD (US)

(73) Assignee: Perinatronics Medical Systems, Inc., Crofton, MA (US)

( * ) Notice: Subject to any disclaimer, the term of this patent is extended or adjusted under 35 U.S.C. 154(b) by 0 days.

(21) Appl. No.: 13/315,234

(22) Filed: Dec. 8, 2011

Related U.S. Application Data

(63) Continuation of application No. 13/234,762, filed on Sep. 16, 2011, now abandoned, which is a continuation of application No. 11/809,876, filed on Jun. 1, 2007, now abandoned.

(60) Provisional application No. 60/809,833, filed on Jun. 1, 2006.

(51) Int. Cl.
*A61B 5/055* (2006.01)

(52) U.S. Cl.
USPC .......................................... 600/413; 600/509

(58) Field of Classification Search
USPC ............................................... 600/413, 509
See application file for complete search history.

(56) References Cited

U.S. PATENT DOCUMENTS

| | | | |
|---|---|---|---|
| 4,310,243 A | 1/1982 | Brown et al. | |
| 4,537,200 A | 8/1985 | Widrow | |
| 4,893,626 A | 1/1990 | Henley et al. | |
| 4,991,580 A | 2/1991 | Moore | |
| 4,991,587 A | 2/1991 | Blakely | |
| 5,038,785 A | 8/1991 | Blakeley et al. | |
| 5,042,499 A * | 8/1991 | Frank et al. | 600/511 |
| 5,436,564 A | 7/1995 | Kreger | |
| 5,511,553 A | 4/1996 | Segalwitz | |
| 5,523,534 A | 6/1996 | Meister | |
| 5,526,813 A | 6/1996 | Yoshida | |

(Continued)

OTHER PUBLICATIONS

F. Odille, C. Pasquier, R. Abacherli, P.-A. Vuissoz, G.P. Zientara, and J. Felblinger, Noise Cancellation Signal Processing Method and computer System for Improved Real-Time Electrocardiogram artifact correction During MRI Data Acquisition, IEEE Transactions on Biomedical Engineering, vol. 54, No. 4, pp. 630-640, Apr. 2007, Institute of Electrical and Electronics Engineers, new York, NY.

(Continued)

*Primary Examiner* — Jonathan Cwern
(74) *Attorney, Agent, or Firm* — Buchanan Ingersoll & Rooney PC

(57) ABSTRACT

High resistance non-metallic ECG leads are used to capture biologically generated electrical signals, and include at least one magnetic resonance noise lead to capture a noise reference signal indicative of electromagnetic noise ambient to the leads generated by magnetic resonance imaging (MRI). The noise reference signal is canceled from the captured electrical signal using an adaptive canceling noise filter to obtain a processed electrical signal indicative of the biologically generated electrical signal that causes movement in a patient's moving body part, such as the heart. A characteristic of the processing electrical signal indicative of the biologically generated electrical signal that causes the movement is detected to obtain a trigger signal, which is then transmitted to cause the MRI system to capture at least one imagine including the moving body part.

14 Claims, 36 Drawing Sheets

(56) References Cited

U.S. PATENT DOCUMENTS

| | | | |
|---|---|---|---|
| 5,917,919 A * | 6/1999 | Rosenthal | 381/71.11 |
| 5,987,348 A | 11/1999 | Fischer | |
| 6,032,063 A | 2/2000 | Hoar | |
| 6,052,614 A | 4/2000 | Morris | |
| 6,070,097 A | 5/2000 | Kreger | |
| 6,201,981 B1 | 3/2001 | Yarita | |
| 7,039,455 B1 | 5/2006 | Brosovich | |
| 2002/0133086 A1 | 9/2002 | Connelly et al. | |
| 2003/0018248 A1 * | 1/2003 | Kreger et al. | 600/413 |
| 2004/0015067 A1 | 1/2004 | Watson | |
| 2004/0225210 A1 * | 11/2004 | Brosovich et al. | 600/372 |
| 2009/0163798 A1 | 6/2009 | Abbott et al. | |

OTHER PUBLICATIONS

J.M. Parker, J.R. aLGER, M.A. Woo, D. Spriggs, and R.M. Harper, "Acquisition of Electrophysiological Signals During Magnetic Resonance Imaging", Sleep, vol. 22, No. 8, pp. 1125-1126, 1999, UCLA, Los Angeles, CA.

H.R. Van Genderingen, M. Sprenger, J.W. De Ridder, A.C. Van Rossum, "Carbon-Fiber electrodes and Leads for Electrocardiography During MR Imaging", Radiology, vol. 171, p. 872, 1989, Free University Hospital Amsterdam, The Netherlands.

M. Yelderman, B. Widrow, J.M. Coiffi, E. Hesler, and J.A. Leddy, ECG Enhancement by Adaptive Cancellation of Electrosurgical Interference, IEEE transactions on Biomedical Engineering, vol. BME-30, No. 7, Jul. 1983.

Guha, S., "Bioengineering in Reproduction Medicine." C CRC Press Boca Raton, FL, 1989, 2 pages.

Kreger, K.S. & Giordano, C.R., Biopotential Adaptive Filtering in an MR Environment. Paper presented at the SMRM 11th Annual Scientific Meeting, 1992, p. 661.

B.J. Mossawir, R.D. Venook, and C.C. Wang, "On the Applicability of the LMS Algorithm to Gradient Noise Elimination from EKG Signals During an MRI Scan", Stanford University, California, 2003.

R. Abacherli, C. Pasquier, F. Odille, M. Kraemer, J.-J. Schmid, and J. Felblinger, "Suppression of MR Gradient Artefacts on electrophysiological Signals Based on an Adaptive Real-time Filter with LMS Coefficient Updates", MAGMA, vol. 18, pp. 41-50, 2005, Springer, Germany.

J. Felblinger, C. Lehmann, and C. Boesch, "Electrocardiogram Acquisition During MR Examinations for Patient Monitoring and Sequence Triggering", Magnatic Resonance Medicine, vol. 32, pp. 523-529, 1994, Wiley-Liss Inc.

J. Felblinger, J. Slotboom, R. Kreis, B. Jung, and C. Boesch, "Restoration of Electrophysiological Signals Distorted by Inductive effects of Magnetic Field Gradients During MR Sequences", Magnetic Resonance in Medicine, vol. 44, pp. 715-721, 1999, University of Bern, Switzerland.

S.E. Fischer, S.A. Wickline, and C.H. Lorenz, "Novel Real-time R-wave Detection Algorithm Based on the Vectorcardiogram for Accurate Gated Magnetic Resonance Acquisition", Magnetic Resonance in Medicine, vol. 42, pp. 361-370, 1991, William & Wilkins, Baltimore, MD.

M.K. Laudon, J.G. Webster, R. Frayne, and T.M. Grist, "Minimizing interference from Magnetic Resonance Images During Electrocardiography", IEEE Transactions on Biomedical Engineering, vol. 45, No. 2, pp. 160-164, Feb. 1998, University of Wisconsin-Madison, WI.

B.J. Mossawir, R. D. Venook, and C.C. Wang, "On the Applicability of the LMS Algorithm to Gradient Noise Elimination from EKG Signals During an MRI Scan," Jul. 29, 2005, Stanford University, CA.

F. Odille, C. Pasquier, R. Abacherli, P.-A. Vuissoz, G.P. Zientara, and J. Felblinger, "Noise Cancellation Signal Processing Method and computer System for Improved Real-Time Electrocardiogram artifact correction During MRI Data Acquisition," IEEE Transactions on Biomedical Engineering, vol. 54, No. 4, pp. 630-640, Apr. 2007, Institute of Electrical and Electronics Engineers, new York, NY.

Guha, S., "Bioengineering in Reproduction Medicine," C CRC Press Boca Raton, FL, 1989, 2 pages.

Kreger, K.S. & Giordano, C.R., "Biopotential Adaptive Filtering in an MR Environment," Paper presented at the SMRM 11th Annual Scientific Meeting, 1992, p. 661.

J. Felblinger, C. Lehmann, and C. Boesch, "Electrocardiogram Acquisition During MR Examinations for Patient Monitoring and Sequence Triggering", Magnatic Resonance Medicine, vol. 32, pp. 523-529, Wiley-Liss Inc., 1994.

B. J. Mossawir, R. D. Venook, and C. C. Wang, "On the Applicability of the LMS Algorithm to Gradient Noise Elimination from EKG Signals During an MRI Scan", accessed on Jul. 29, 2005, link: http://www.stanford.edu/~darkside/mywork/ee373finalreport.pdf.

Extended Search Report from European Patent Office dated Jul. 5, 2013, issued in corresponding European Patent Application No. 13156941.0. (6 pages).

* cited by examiner

Carbon Wire Diagram

Carbon Wire Diagram

Carbon Wire Diagram

Carbon Wire Picture

Fiber Optics Amplifier and Transmitter Picture

Fiber Optics Receiver Picture

ECG TRIGGERED HEART AND ARTERIAL MAGNETIC RESONANCE IMAGING

This application is a continuation of U.S. patent application Ser. No. 13/234,762, filed Sep. 16, 2011 now abandoned, which is a continuation of U.S. patent application Ser. No. 11/809,876, filed on Jun. 1, 2007 now abandoned, which claims the priority benefit of U.S. Provisional Application No. 60/809,833, filed Jun. 1, 2006, which are hereby incorporated by reference in their entirety.

GOVERNMENT LICENSE RIGHTS

This invention was made with government support under Grant HL66791, awarded by the National Institutes of Health. The government has certain rights in the invention.

BACKGROUND OF THE INVENTION

Magnetic resonance imaging of hearts and connected blood vessels is the gold standard of determining pericardial structure, disease and function of the heart and its major connected vessels.

Hearts and blood vessels are in constant motion and collecting, pooling and emptying of blood presents difficulty in stable imaging. The beating of the heart and movement of the heart and blood vessels may be regular or irregular and may be from about 70 to 150 or more beats per minute during imaging, with fluctuations of 30 beats per minute or more. Consequently it is difficult to obtain precise magnetic resonance images of the heart and its connected vessels for study and comparison.

Needs exist for improved magnetic resonance imaging.

BRIEF SUMMARY OF THE INVENTION

The invention provides new and improved acquisition, transmission, processing, and detecting systems to control triggering of magnetic imaging for producing images of the heart and principal arteries, which are subject to movement during pulsing.

DETAILED DESCRIPTION OF THE PREFERRED EMBODIMENTS

Overview of Preferred Embodiment

Figure 1:
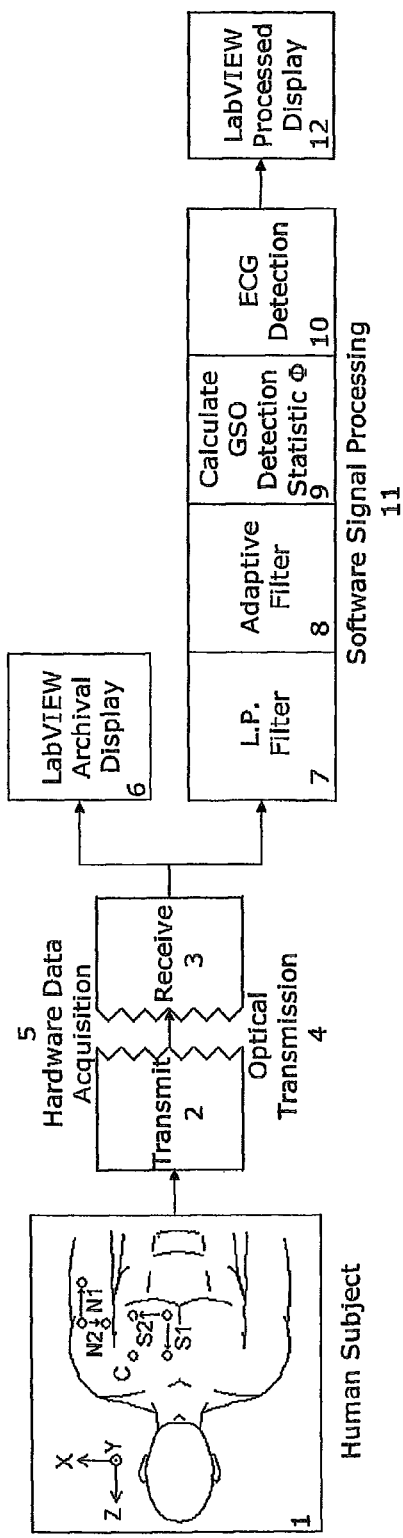
FIG. 1 is a block diagram of the entire ECG cardiac gating process showing the magnetic imaging system and the transmission and processing aspects of the invention.

The preferred embodiment, shown in FIG. 1, consists of electrodes placed on the chest and arm of a human subject 1. A hardware data acquisition system 5 acquires the electrocardiogram and electrocardiographic noise from the chest and arm electrodes and optically transmits 2, 4 those signals out of the MRI scanner. Outside of the MRI scanner, these signals are received 3, converted back to electrical signals, and the data archived to a LabVIEW archival display computer program 6. In addition, these signals are concurrently processed by a number of software signal processing modules 11. The software signal processing consists of a low pass filter 7, one of various adaptive filters 8, a module that calculates a detection statistic using a GSO vector 9 and a module that performs ECG detection 10 and transmits a signal to the MRI to emit MR gradient pulse sequences and an RF signal to produce images. Finally, the detected electrocardiogram signal is depicted in a LabVIEW computer program display 12.

Figure 32:
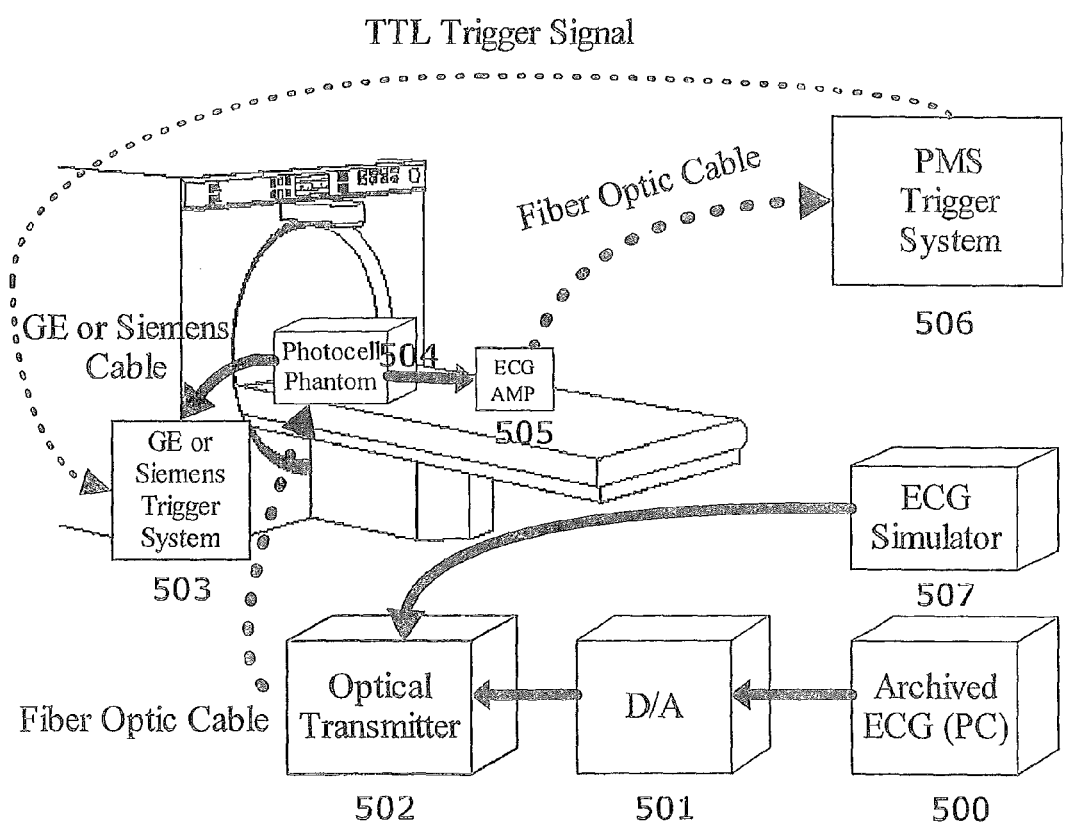
FIG. 32 shows an overview of the experimental setup used to evaluate the performance of Perinatronics ECG trigger system. In the experimental setup, either actual archived or simulated ECG data is optically transmitted to a phantom within the scanner.

FIG. 32 shows an overview of an experimental setup. ECG is simulated by using archived ECG 500 and a digital to analog converter (D/A 501), or from an ECG simulator 507. Simulated ECG is then sent to an optical transmitter 502 which sends it to the scanner via fiber optic cables 509, where it is injected into a phantom 504. The phantom 504 is connected to an ECG amplifier 505 which transmits the ECG signals via fiber optic cables 510 to our triggering system 506 which then processes the signals and transmits TTL triggering signals 508 back to the MRI triggering system 503.

In the acquisition steps of the present invention, different kinds of leads are provided to avoid electrical noise in the leads produced by magnetic fields and pulsing and shifting of magnetic fields during magnetic resonance imaging. Since the leads are connected to probes on the human subject 1 within magnetic resonance machines, it is necessary that the leads collect as little electrical noise as possible from induction by shifting and pulsing magnetic fields to provide a high signal-to-noise ratio and do not heat up sufficiently to subject the patient. The preferred leads are carbon filament wires within relatively thick insulation, and without metallic inclusions in the wires or in the insulation. The leads are as short as possible to avoid and reduce interference.

Ends of the carbon filament leads are connected to a transmitter 2 near the human subject 1 within the magnetic resonance imaging scanner. Electronics in the transmitter 2 amplify the ECG signals and convert the amplified ECG signals to optical signals, changing voltage in the ECG signals to frequencies in the optical signal wavelength. The optical pulses are transmitted 4 through optical fibers or through the air to receivers 3 in the data acquisition hardware 5.

Electrodes on the human subject's chest and arm are connected by the same carbon filament leads of the same short lengths to the transmitter 2. The purpose of the arm electrode and connected leads is not to conduct ECG signals to the transmitter 2 in the magnetic resonance scanner, but rather to pick up and conduct noise signals. The noise signals are collected directly from leads connected to the human subject's 1 body and are not collected from the imaging equipment. The detected voltage noise signals from the carbon fiber leads attached to the chest and arm electrodes are converted in the transmitter 2 to optical frequency signals and are transmitted through optical fibers or through the air to the receiver 3 outside of the magnetic resonance imaging equipment.

The optical signals received 3 outside of the magnet either through the air or optical fibers are sent to a software signal processor 11 outside of the magnetic resonance imaging scanner. The processor operates on the signals picked up from the chest, and using the noise signals picked up from the chest or arm leads, adaptively cancels the noise. Adaptive cancelling noise filters, such as least mean squares (LMS), recursive least-squares (RLS) and least-squares lattice (LSL) filters, use the noise signals picked up from the extra leads attached to the electrodes on the human subject's chest or arm to cancel noise from the chest electrodes and leads.

In the software signal processor 11, after noise is filtered 7, 8, the Gram-Schmidt Orthogonalization (GSO) 9 vectors are formed and derivatives of the ECG signal are taken to detect 10 the rising edge of the R wave within the ECG signal as soon as possible to trigger the transmission of the MRI magnetic gradient pulse sequences to produce precise images of the heart and primary vessels at times in the heartbeat cycle.

ECG Leads

A preferred embodiment uses high resistance non-metallic ECG leads. While conventional cables for acquiring ECG signals within the MR scanner have successfully dealt with the concerns of patient heating, they are very fragile, cumbersome and expensive. The usual practice for GE, Philips and Invivo has been to utilize this six foot distributed lead wire harness assembly with an additional ten feet of cabling which incorporates a set of delicate lead wires. Each lead wire has a fragile nichrome wire, helically wound on a bundle of glass that is then surrounded by a thermally insulating jacket. This arrangement provides a high resistance to each lead wire, so that eddy currents generated by the RF energy within the magnet are reduced without heating the subject.

The present invention is based primarily on the consideration of patient safety and the potential for RF heating effects and image artifacts caused by the induction of eddy currents within the ECG leads by the time-varying MR gradients. Both of these effects are diminished by reducing the amplitude of the eddy currents which are inversely proportional to the resistance of the conductor.

Figure 2A:
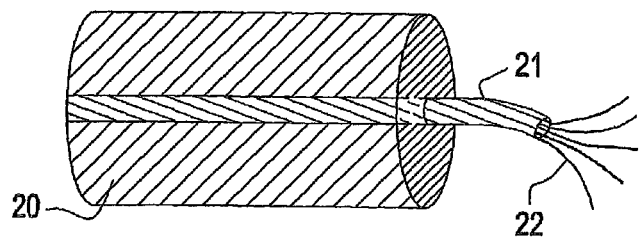
FIG. 2 is a diagram of carbon leads to conduct the ECG signal within the MRI.
Figure 2B:
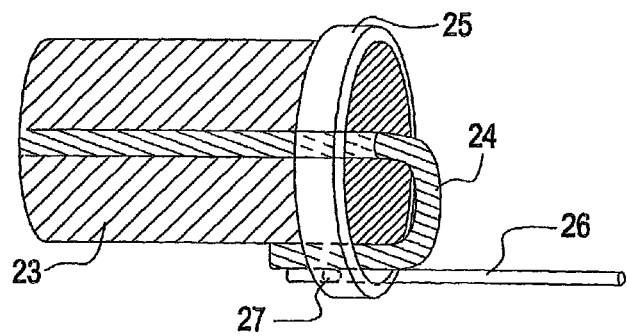
Figure 33:
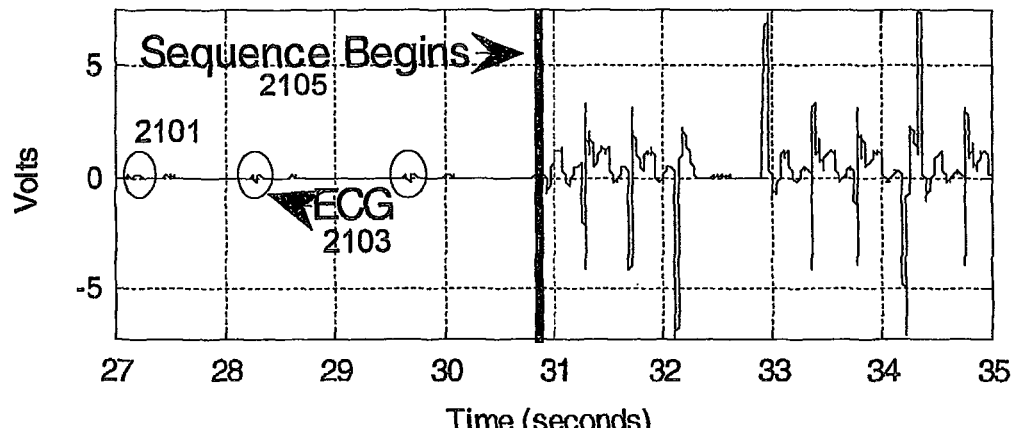
FIG. 33 shows the SNR improvement of fiber optics data transmission versus conventional cable use. The top trace illustrates the sheer magnitude of gradient artifacts introduced via the GE cabling system. The GE lead wires caused the amplitude of the artifacts to be several orders of magnitude greater than the ECG signal. The optical system, with short carbon fiber leads, resulted in artifacts being only twice the amplitude of the ECG.
Figure 33:
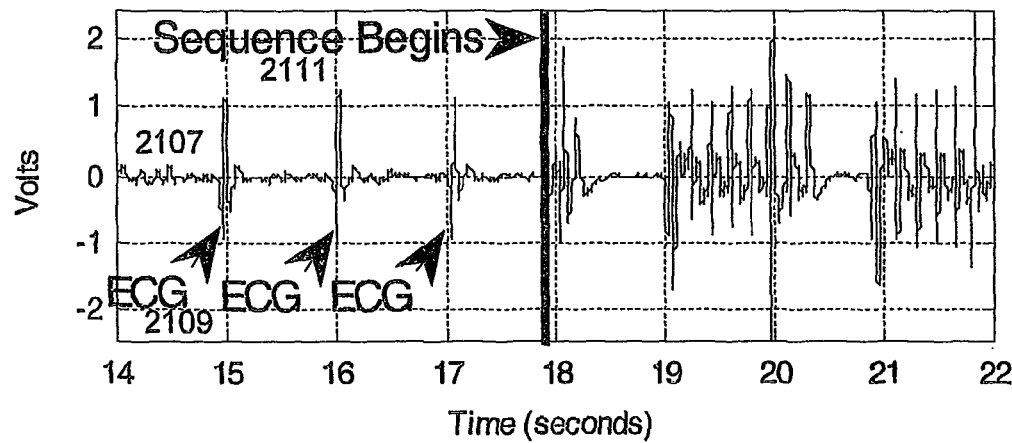

A preferred embodiment uses an MR compatible ECG lead system of a considerably different design, illustrated in FIG. 2A-2C and 13, the effectiveness of which has been demonstrated in clinical testing and is shown in FIG. 33. The top trace 2101 shows the ECG 2103 recorded with conventional (GE) leads, while the bottom trace 2107 shows ECG 2109 data acquired with PMS optical cable. As the sequence begins 2105, 2111, each trace shows the additional artifacts mixed with the ECG signals. This lead system uses short (12 in.) lengths of high resistance carbon impregnated fiberglass material in FIG. 2A. The fiberglass 22 is wrapped with a conductive acrylic latex sheath 21 providing a distributed impedance of approximately 8.6K ohms/foot. In addition, an overall silicone rubber jacket 20 provides thermal resistance. FIG. 2B shows the distal end of the high resistance carbon impregnated material wire 23 with an attached electrical connector 26, 27. The electrical plug connector consists of an approximate 2" copper wire gauge #14 26. That wire 26 is soldered at connection 27 to a brass ring 25 of approximately 8 mm in diameter and approximately ⅛ inch width. Following the connection of 26 with 25, the ring is placed over the silicon rubber jacket and is physically crimped to electrically connect wire 26 to an approximate ½ inch length of the conductive acrylic latex sheath 24.

Figure 2C:
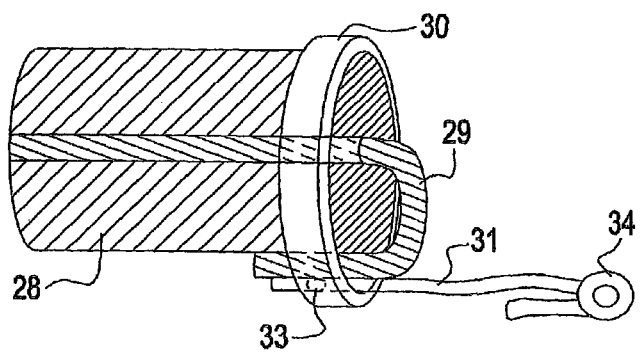

FIG. 2C shows the proximal end of the ECG carbon wire 28 with an attached ½ inch copper wire 31 ECG and connector 34. The electrical connector at the distal end is assembled in a fashion similar to that previously described for the end shown in FIG. 2B. More specifically, FIG. 2C shows an electrode connector 34 and its connecting copper wire 31 soldered at connection 33 to a brass ring 30 and later crimped to make a good electrical connection with the conductive acrylic latex sheath 29.

In a 1.5 T magnet this ECG lead assembly did not indicate a temperature exceeding 37° C. on a Thermax Level 8 surface temperature indicator strip. This material is not fragile or cumbersome to work with in patient monitoring; it is also inexpensive.

Transmission

Figure 3:
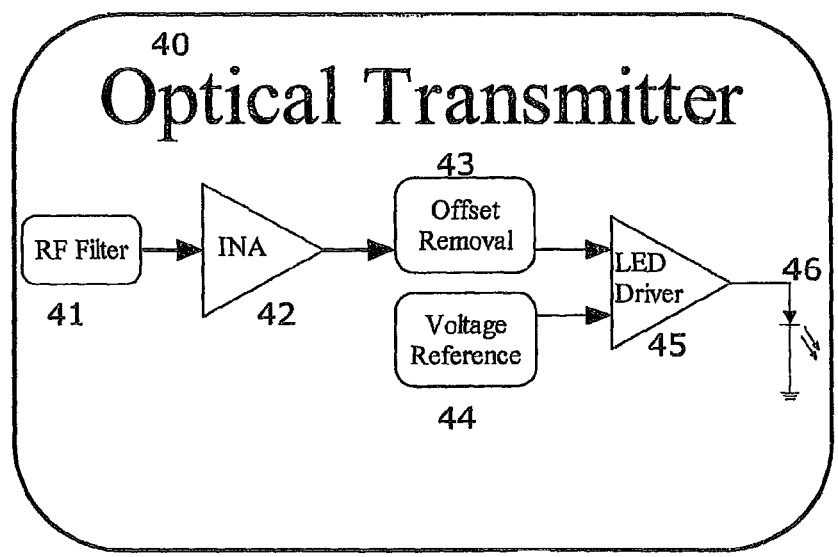
FIG. 3 is a diagram of the ECG data transmission hardware.
Figure 3:
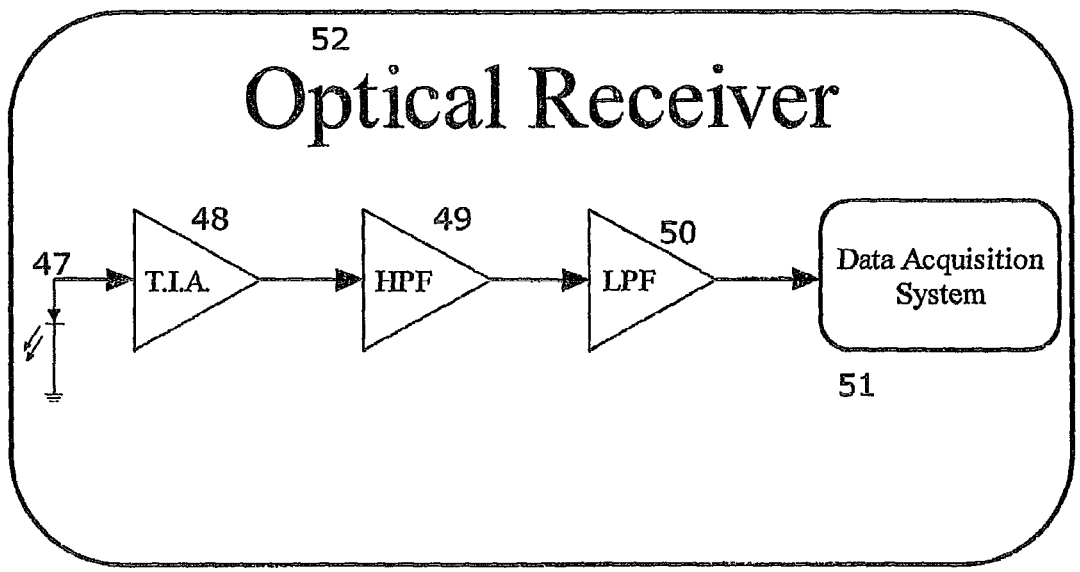

A preferred embodiment, as shown in FIG. 3, uses a low cost light emitting diode (LED) optical transmission design. This optical ECG transmission system provides a means of transmitting ECG signals from the MR scanner which substantially mitigates the MR scanner's electromagnetic interference, has the potential to be "wireless", i.e., no fiber optics, and is simple and inexpensive. The system uses an LED analog transmission system and is therefore much less complex and less expensive than a digital system would be. FIG. 3 shows an optical transmitter 40 and an optical receiver 52. More specifically, the optical transmitter 40 consists of an RF filter 41 and instrumentation amplifier 42, a means to provide a voltage offset removal 43 from the instrumentation amplifier, a voltage reference 44 for the LED driver 45, and finally, the LED transmitter 46. The specific details of the optical receiver 52 consist of a photodiode detector LED 47, a transimpedance amplifier 48, a high pass filter 49, a low pass filter 50, followed by a data acquisition system 51. The transmitter LED 46 and receiver photodiode detector LED 47 are a matched pair supplied by Industrial Fiber Optics, Inc.

We have established the following specifications for our MRI ECG data acquisitions and optical transmission system: 1) an instrumentation amplifier (INA) based ECG amplifier 2507, 2) INA gain between 1 and 50, and 3) INA AC coupled to LED-based fiber optics transmitter.

Figure 14:
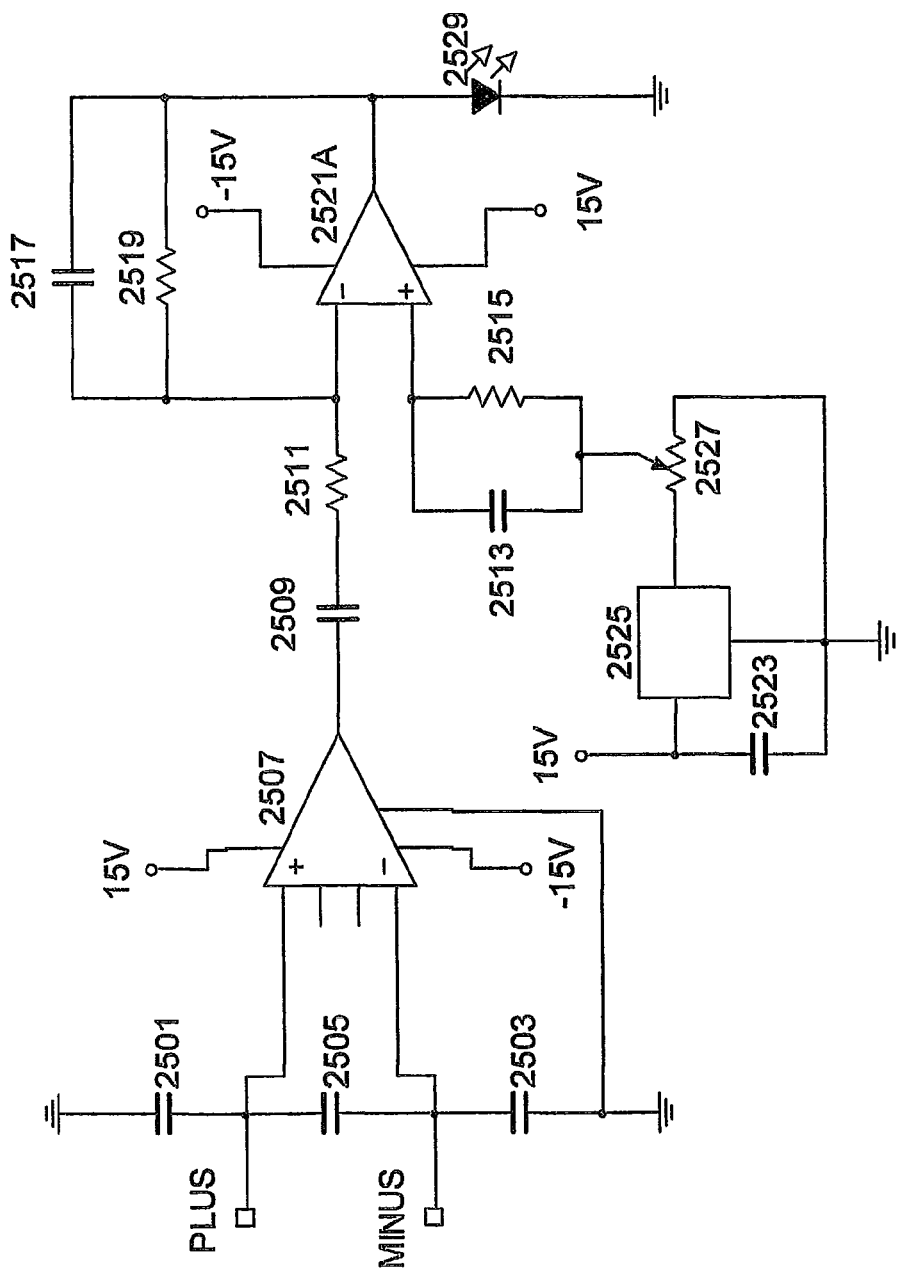
FIG. 14 is an electronic schematic diagram of the MRI compatible ECG amplifier and transmitter.

FIG. 14 shows the electrical schematic diagram of the amplification and transmission modules. Unnecessary details, such as decoupling capacitors and other construction-related items, have been left out for clarity. Four to six channels are constructed. The INA (Texas Instruments INA128, or Analog Devices AD8221) are chosen for its superb common mode rejection capability (~130 dB). Capacitors 2501, 2503 and 2505, in combination with the high resistance of the carbon fiber ECG leads, form an RF filter with a low pass cutoff at approximately 8 KHz, which is orders of magnitude below the MR and RF-coil excitation frequencies.

Figure 15:
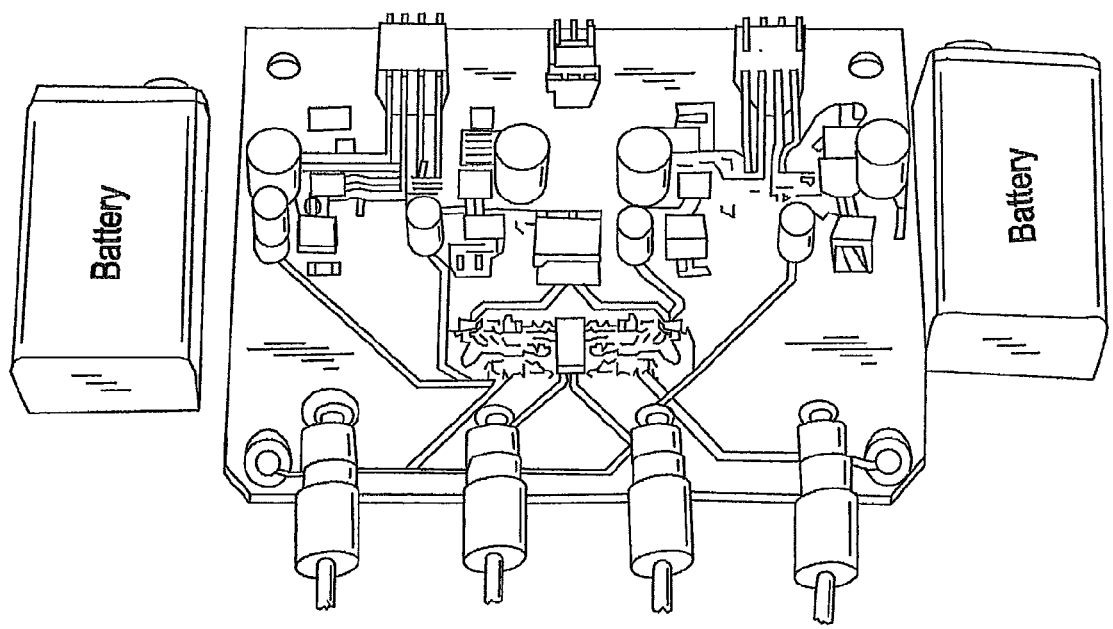
FIG. 15 is a photograph of the four-channel ECG amplifier and fiber optics transmitter with MR compatible lithium batteries fabricated with surface mount components.

The output of the INA is capacitor 2509 coupled to a differential amplifier (OPA4277) which serves as the LED driver. Capacitor 2509 and resistor 2511 act as a high pass filter to ensure that spurious offsets from the INA do not influence the bias-point of the LED, which is independently controlled by potentiometer 2527. The reference for the LED bias is derived from a voltage reference source 2525 which allows the batteries to be virtually exhausted without affecting the quality of the transmitted ECG signal. Capacitor 2523 removes the high frequency of the supply. In an alternative embodiment, power is piped in over an optical fiber, using a laser diode and miniature solar cells as the power source. A photograph of the amplifier and fiber optics transmitter is shown in FIG. 15.

The LED driver consists of operational amplifier OPA4277, 2521A together with low pass filters consisting of RC combinations of 2517, 2519 and 2513, 2515 respectively.

In a preferred embodiment, the transmitter LEDs 2529 are low power red 660 nm wavelength and the receiver accepts power from the real-time computer system. The printed circuit boards of both the transmitter and receiver are designed to reduce their size and eliminate as much metal as possible.

Reception

In a preferred embodiment, a low cost LED optical receiver is used. An optical ECG data receiver placed outside the scanner room includes a photodiode-based transimpedance amplifier with easily adjustable gain, high-pass analog filter (2-pole Butterworth with 1-5 Hz cutoff), and low-pass analog filter (multi-pole Butterworth with 35-200 Hz cutoff).

Figure 20:
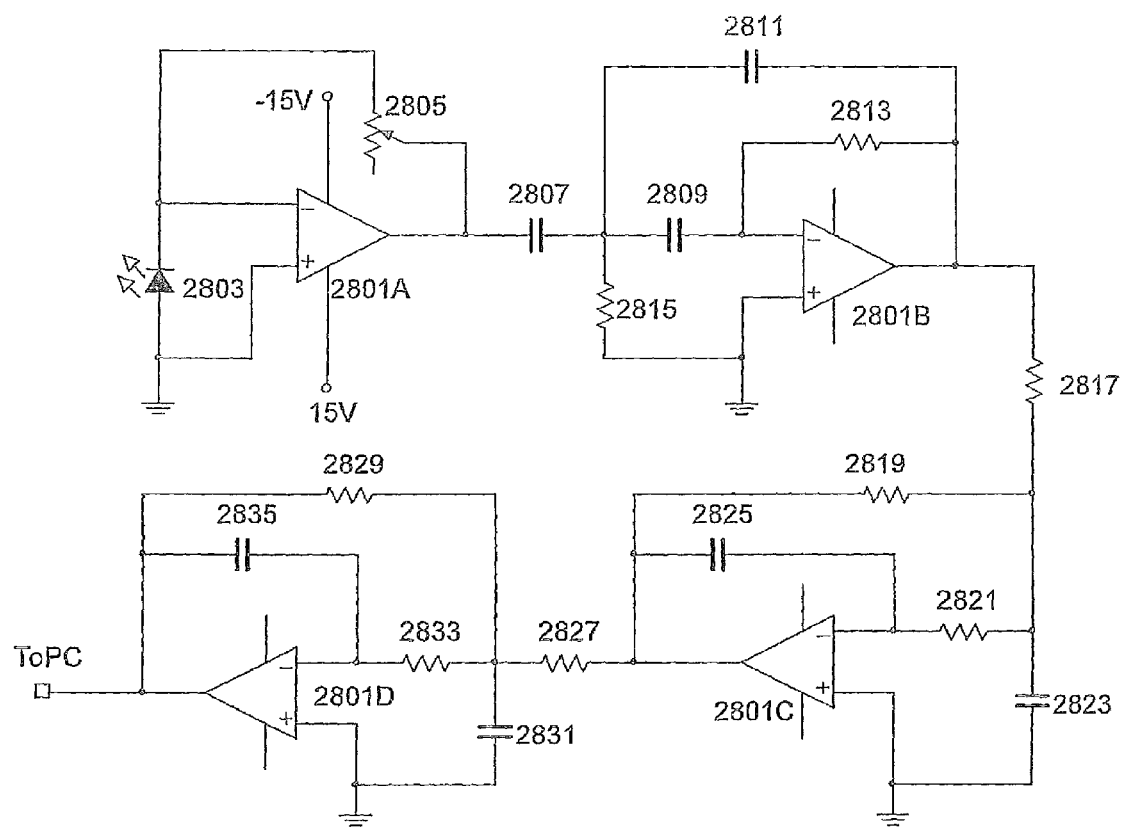
FIG. 20 is a schematic diagram of the ECG receiver showing the photodetector (LED1), transimpedance amplifier (U1A) and analog filters.

FIG. 20 shows the electrical schematic diagram of the ECG receiver. The receiver photodetector LED 2803 circuit is a low-gain transimpedance amplifier 2801A. The low gain, which can be adjusted via potentiometer 2805, is acceptable because of the brightness of the transmitter LED and the efficiency of the fiber optics coupling (total length <30 feet). The transmitter and receiver can be coupled through approximately 25 feet of 1 mm plastic optical fibers (Industrial Fiber Optics, Inc. IF-E90 & IF-D90 series). It is desirable to maintain a low gain on the transmitter amplifier because the input signal voltage can be very large due to the large gradient switching artifacts and a high gain would lead to signal clipping.

The photodiode amplifier in the receiver is followed by high-pass and low-pass filters. The high-pass filter consisting of an op amp 2801B and discrete RC components 2807, 2809, 2811, 2813, 2815 is a two-pole Butterworth filter with 1-5 Hz cutoff. This filter is very effective in reducing some (and, in some cases, all) of the magneto hydrodynamic (MHD) artifact from the ECG ST segment and T-wave as shown in FIG.

22. The MHD artifact 1001 can be virtually eliminated 1003 by judicious electrode placement and by raising the high-pass filter cutoff to 5.0 Hz. These simple maneuvers solve the MHD artifact problem in detection of the ECG R-wave.

Figure 21:
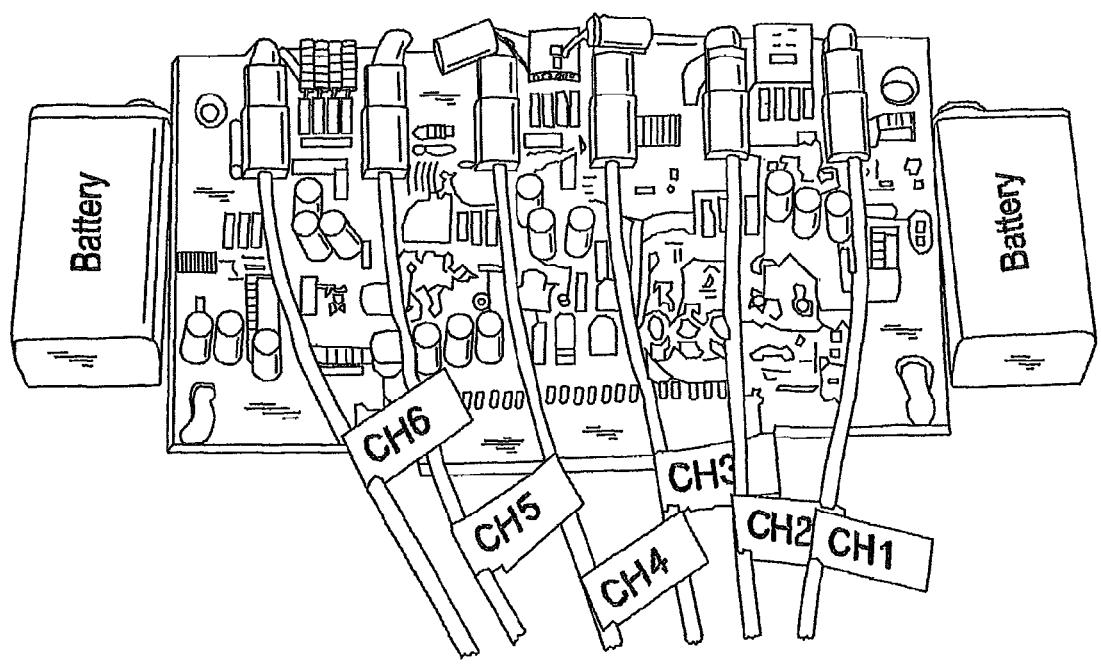
FIG. 21 is a photograph of a six-channel LED optical receiver with lithium batteries.
Figure 22:
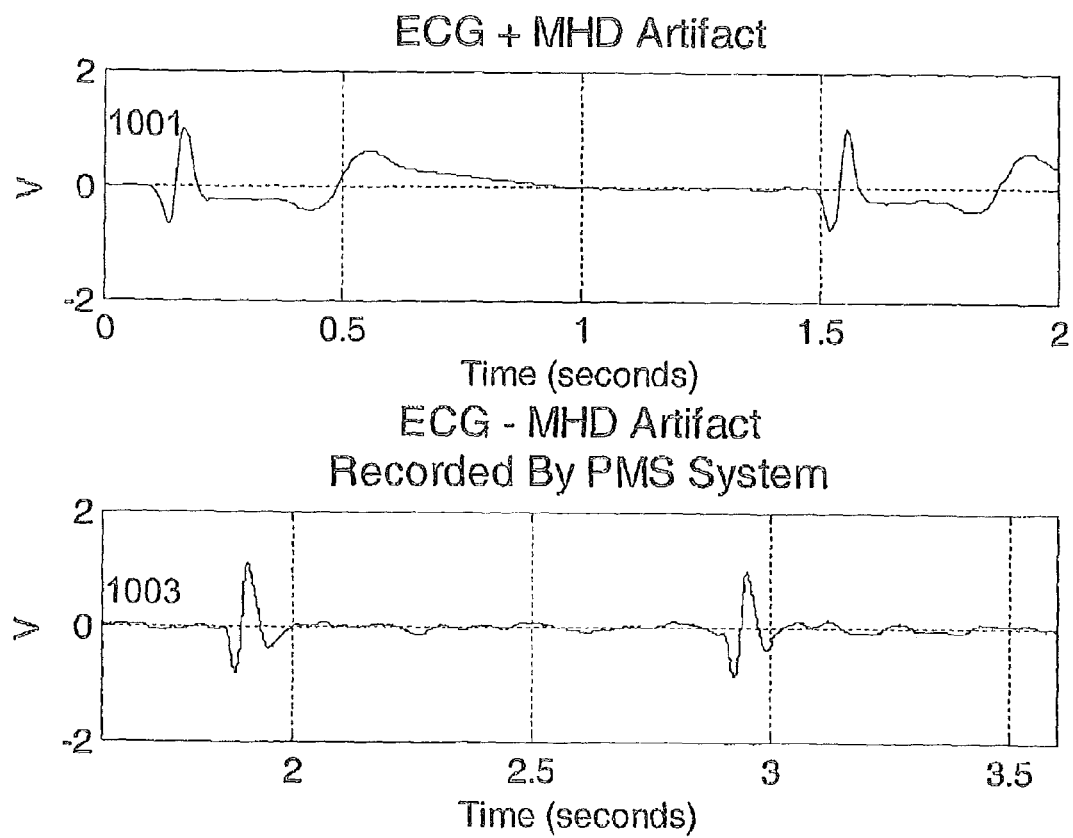
FIG. 22 illustrates the magnitude of the magnetohydrodynamic (MHD) artifact. In this case the electrodes were positioned in accordance with the standard diagnostic ECG convention. The standard ECG amplifier response (0.05-100 Hz) leads to an artifact that can be greater in magnitude than the QRS complex.

The low-pass filter consisting of op amps 2801C-D and discrete RC components 2817, 2819, 2821, 2823, 2825, 2827, 2829, 2831, 2833 and 2835 is also a multi-pole Butterworth design with a frequency cutoff range between 35 and 200 Hz, which also serves as an anti-aliasing filter for the data acquisition system which follows the receiver. The values have been determined to be optimal through a series of alternate designs. The relatively wide latitudes in gain and cutoff frequencies in the ECG transmitter and receiver have allowed a flexible design. This latitude is easily justified by the wide dynamic range and power of the digital signal processing capabilities of the computer algorithm. A photograph of the ECG optical receiver is shown in FIG. 21.

Analog-to-Digital Conversion, Data Acquisition and Data Archival Methods

Several channels of ECG, RF, and gradient artifact noise are acquired and transmitted into the control room to the data acquisition system. The output from each channel of the optical receiver connects to a Personal Computer Memory Card International Association (PCMCIA) analog-to-digital converter module by means of a 50-pin ribbon cable. The data is digitized to 16 bits using a Computer Boards (now Measurement Computing Corp., Middleboro, Mass.) PCMCIA card PC-DAS16/16-AO and each channel is sampled at, for example, 4098 samples/second. The data can be collected and archived using a data acquisition application designed using LabVIEW 7 Express, which can be executed on a Dell Inspiron 8600 laptop computer.

Digital Signal Inputs

As shown in FIG. 1, four or six channels of data are collected using the data acquisition hardware. In one embodiment, two channels from the patient's chest (S1 and S2) and two from the arm (N1 and N2), collected at 4098 samples/second, for example, provide sufficient data fidelity to successfully isolate the respiration and ECG R waves, though another embodiment with a third set of channels (S3 and N3) provides greater accuracy.

Figure 25:
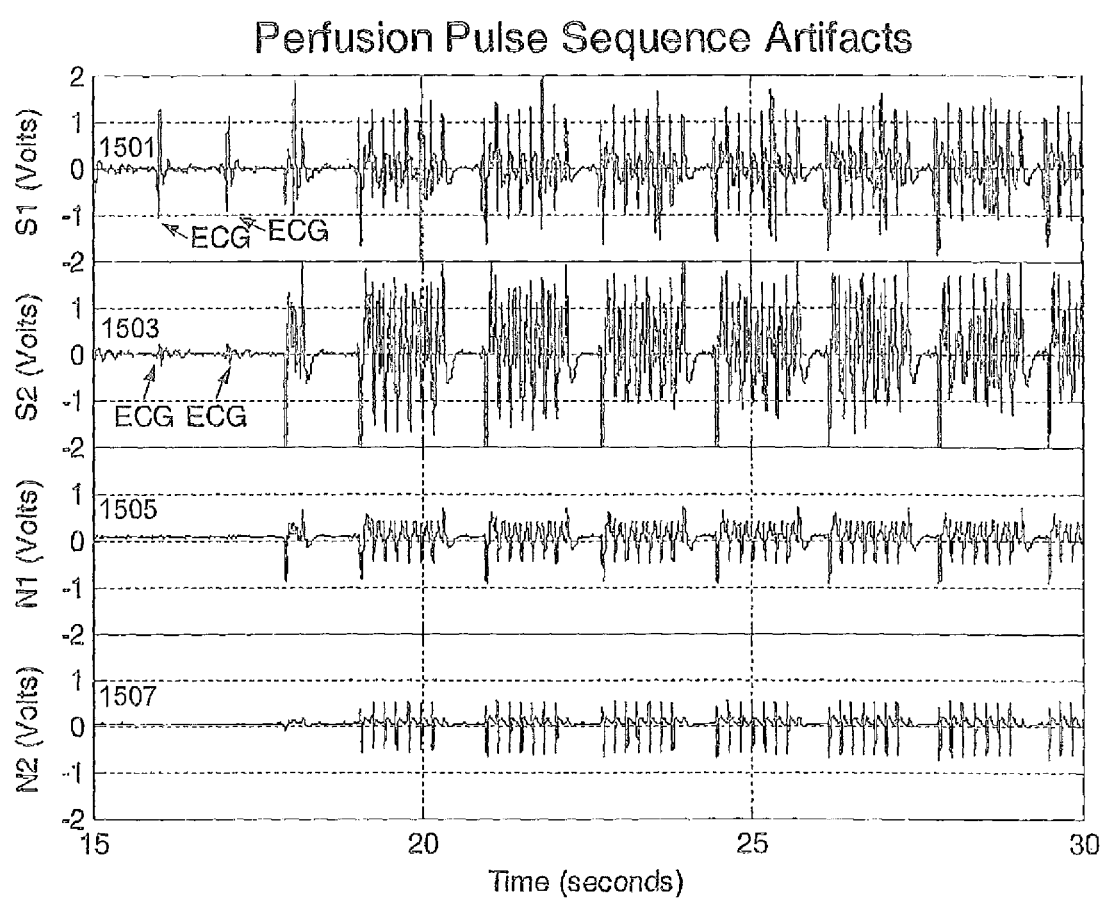
FIG. 25 shows ECG data recorded during an MRI scan using the Perfusion Pulse Sequence. Channels S1 and S2 show ECG and MR artifact data recorded from two chest leads. Channels N1 and N2 show the artifacts (only) recorded from two channels on the subject's arm. Note the small magnitude of the ECG signal in channel S2.

FIG. 25 illustrates that different anatomical positions of the ECG electrodes on the chest, labeled as channel S1 and channel S2, produce quite different ECG recordings 1501, 1503, while both channels have the same gain. For this reason, the GSO vector lead system is utilized to provide the vector sum of these two ECG signals. Poor signal-to-noise ratio is also evidenced in FIG. 25. FIG. 25 also shows two additional recorded channels of magnetic gradient artifact alone, labeled as channel N1 and channel N2 1505, 1507. This data was recorded from the subject's arm during the MR imaging scan.

Figure 26:
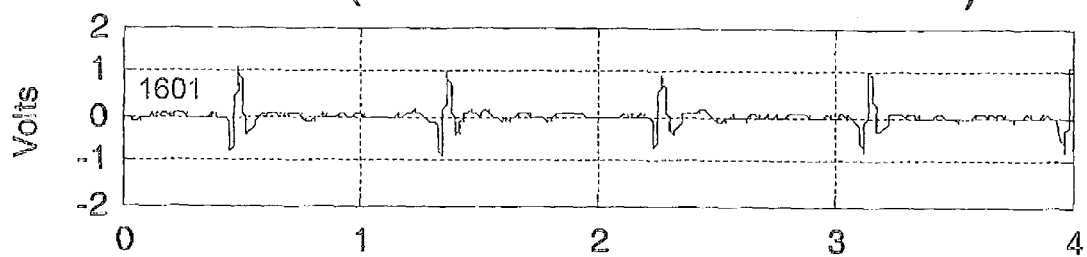
FIG. 26 shows an ECG signal collected before and during a Perfusion pulse sequence. The lower tracing shows every other ECG complex is corrupted by noise.
Figure 26:
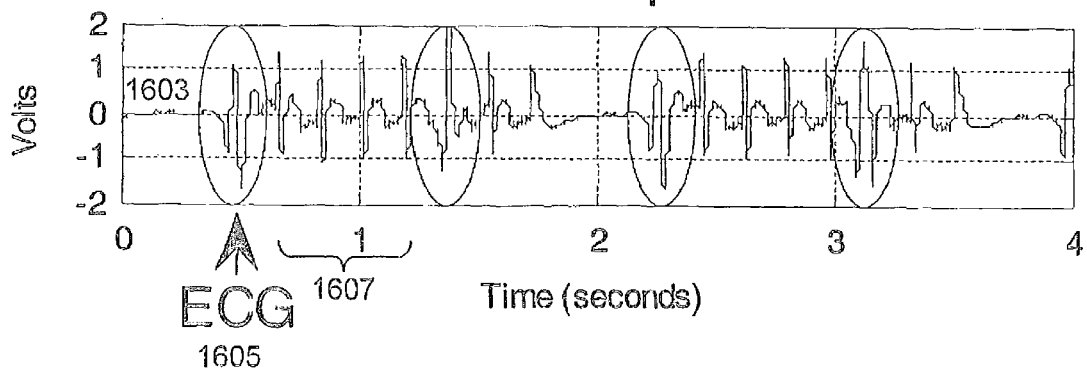

FIG. 26 shows an expanded time course of a 4-second portion of ECG data from the same subject. The upper trace shows a record of the ECG (alone) prior to MR image scanning, i.e., without magnetic gradient artifacts 1601. The data in the lower trace was collected during an MR imaging scan using the perfusion pulse sequence 1603. The lower tracing shows that the gradient amplitudes 1607 are of such a significant magnitude that detection of the ECG complexes 1605 would be virtually impossible without additional digital signal processing.

Different sampling rates are available, with lower rates requiring less processing speed and higher rates providing greater accuracy but requiring greater processing speed for real-time implementation. All signals are received from within the magnet and transmitted to a computer outside the MRI scanner. The signals are archived to hard disk and displayed.

FFT and FIR Digital Filtering

Now, since most of the power of the ECG is in the 5-30 Hz bandwidth, frequencies above 30 Hz are safely filtered out without seriously distorting the ECG. The hardware data acquisition system already includes an analog anti-aliasing low pass filter with a 100 Hz cutoff frequency to begin to attenuate the large magnitude high frequency artifacts. In order to implement the required filtering in a real time environment as is required for triggering in a preferred embodiment a Finite Impulse Response (FIR) digital filter design is employed. One such filter is a hamming window-based, discrete-time, direct-form, FIR filter design with a cutoff frequency of 30 Hz.

Figure 27:
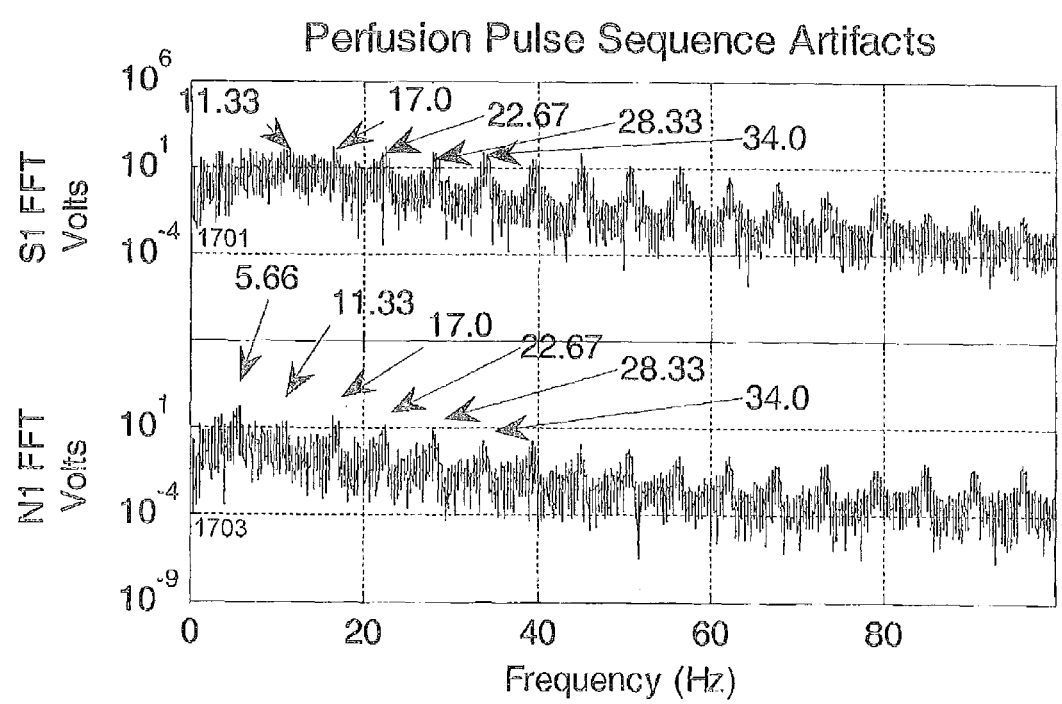
FIG. 27 shows a Frequency plot of MR artifacts from perfusion MR Pulse Sequence (Log. Scale). Note that the noise channel (N1) shows frequencies in the ECG bandwidth (5-30 Hz).

The top trace 1701 in FIG. 27 shows the spectrum, on a logarithmic scale, of the ECG plus magnetic gradient artifacts. The lower trace 1703 shows the spectrum of the magnetic gradient artifacts alone. Most of the power of the ECG is in the 5-30 Hz bandwidth. As can be seen from the figure, the MR gradient artifact noise pulse sequence spectrum completely overlaps the diagnostic ECG spectrum. Since these harmonics completely mask the ECG complex, it is not possible to extract the ECG complex from the magnetic gradient artifacts using traditional frequency filtering.

Figure 28:
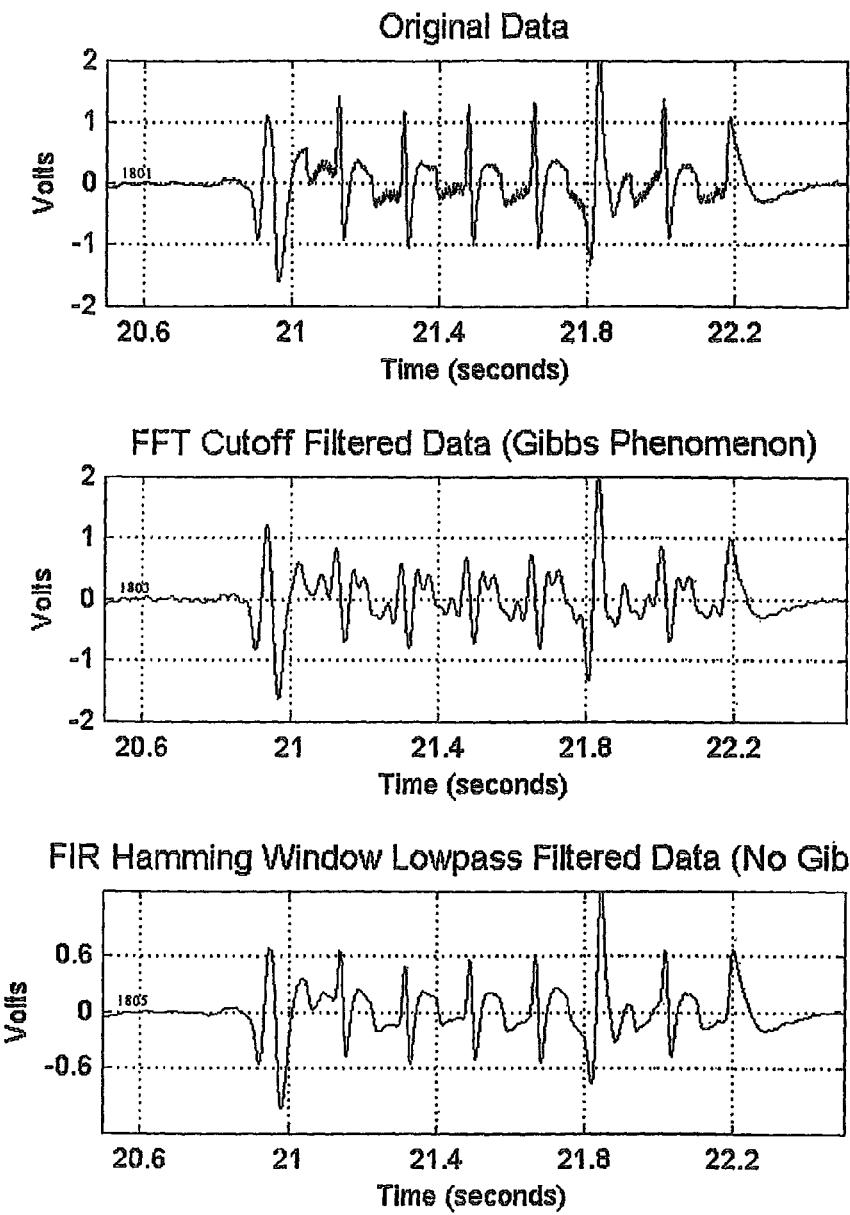
FIG. 28 shows an ECG signal and MR artifact data obtained from the subject undergoing MRI scan using perfusion pulse sequence: a) data as recorded with 100 Hz anti-alias low-pass filtering; b) data as filtered with 30 Hz FFT displaying minor oscillatory behavior in the response, and c) data as processed using a weighted FIR filter.

FIG. 27 illustrates that by viewing the MR artifact noise in the frequency domain, it becomes apparent that the MRI introduces a "fundamental" noise frequency with many harmonics. These interfering frequencies are discrete and defined by the loop structure in the MR imaging pulse sequences. The fundamental frequency of each MRI pulse sequence varies, but is determined by the repetition rates of any given sequence. The fundamental frequency of the Perfusion scan is at 5.66 Hz, as shown in FIG. 27, with harmonics at 11.33, 17.0, 22.67, 28.33, 34.0 Hz, etc. This artifact noise is within the base band and is not aliased. FIG. 28 shows an ECG signal and MR artifact data obtained from the subject undergoing MRI scan using perfusion pulse sequence: a) data as recorded with 100 Hz anti-alias low-pass filtering 1801; b) data as filtered with 30 Hz FFT displaying minor oscillatory behavior in the response 1803, and c) data as processed using a weighted FIR filter 1805.

Adaptive Filtering Methods

Figure 4:
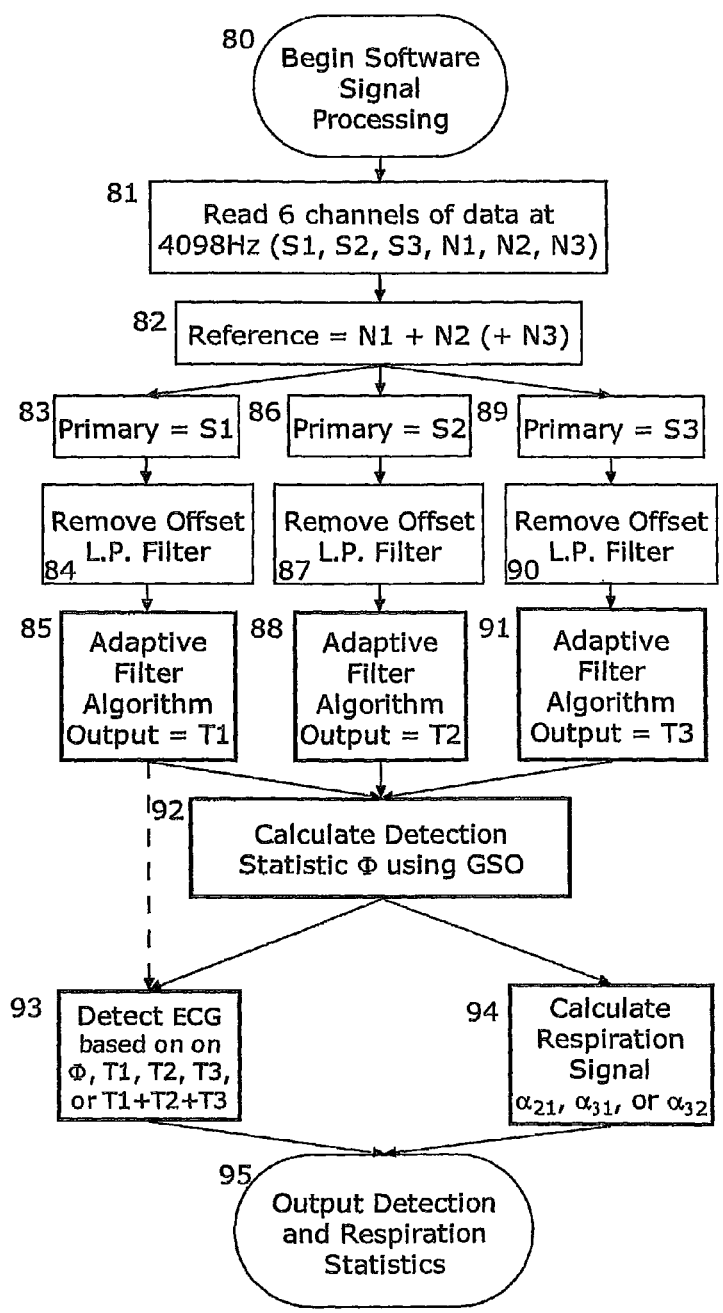
FIG. 4 is a flowchart representation of the software signal processing of FIG. 1.
Figure 5:
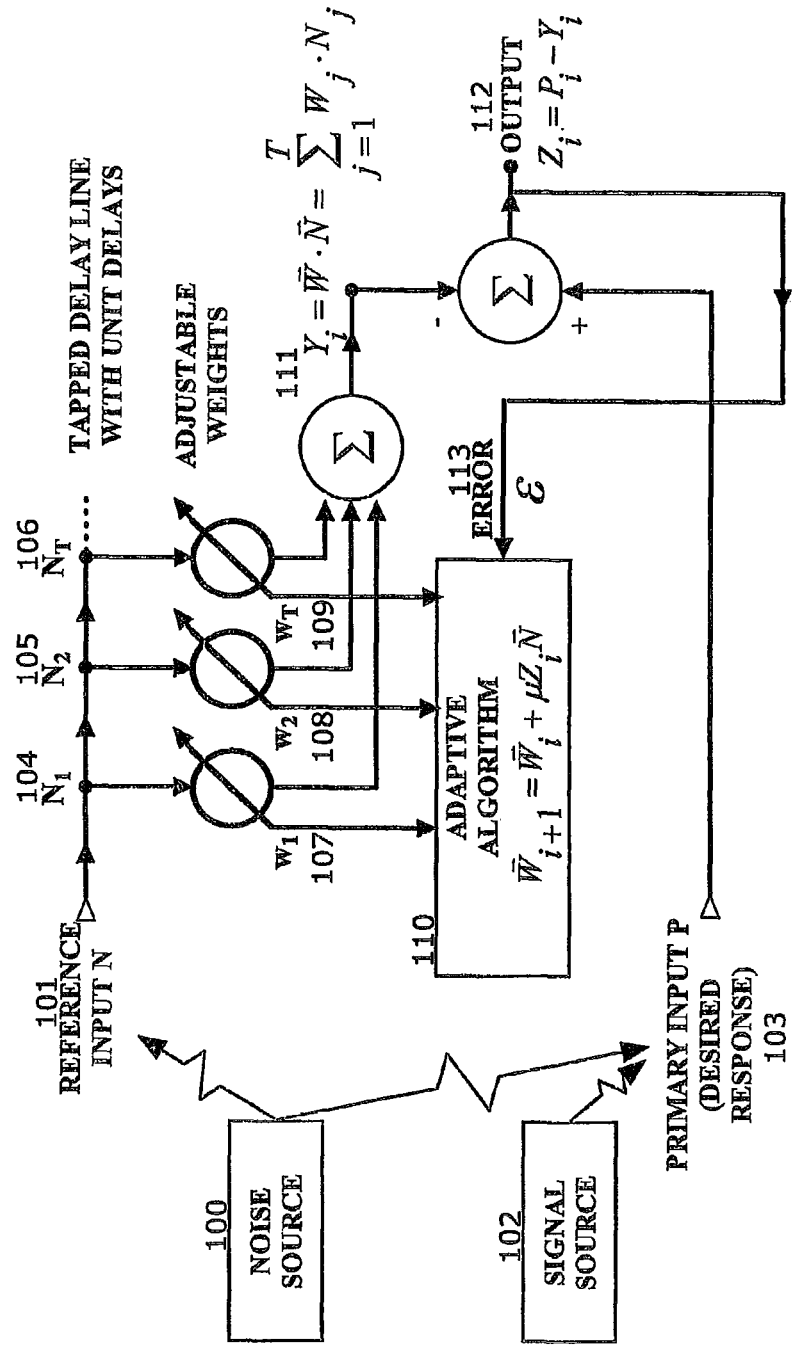
FIG. 5 is a detailed block diagram of the LMS adaptive filter of FIG. 4.
Figure 6:
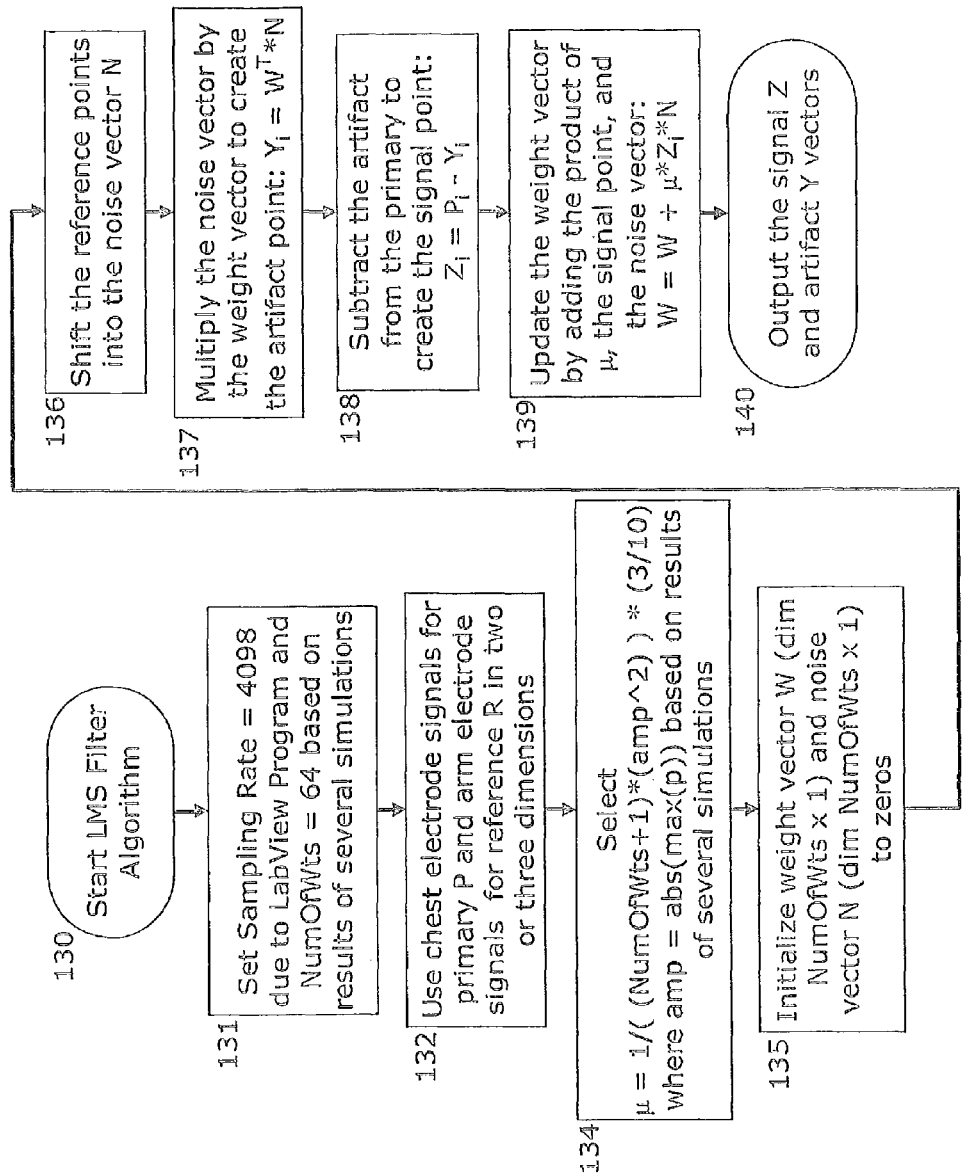
FIG. 6 is a flowchart of the LMS adaptive algorithm of FIG. 4.

A least mean square (LMS) adaptive noise cancellation filter illustrated in a block diagram in FIG. 4 and FIG. 5, and in a detailed flow chart in FIG. 6, is used to cancel the noise created by the time-varying MR gradient artifacts that occur in the same frequency band as the ECG data. S1, the low-pass frequency filtered data as described above and shown by 81 and 132, is the primary input into the least mean square (LMS) filter. The application of the least mean square (LMS) adaptive noise cancellation filter also requires access to a "noise reference." This noise reference can be obtained either from one set of chest electrodes in which the ECG signal is relatively weak or obtained by simply attaching additional ECG electrodes to one of the subject's arms.

Figure 34:
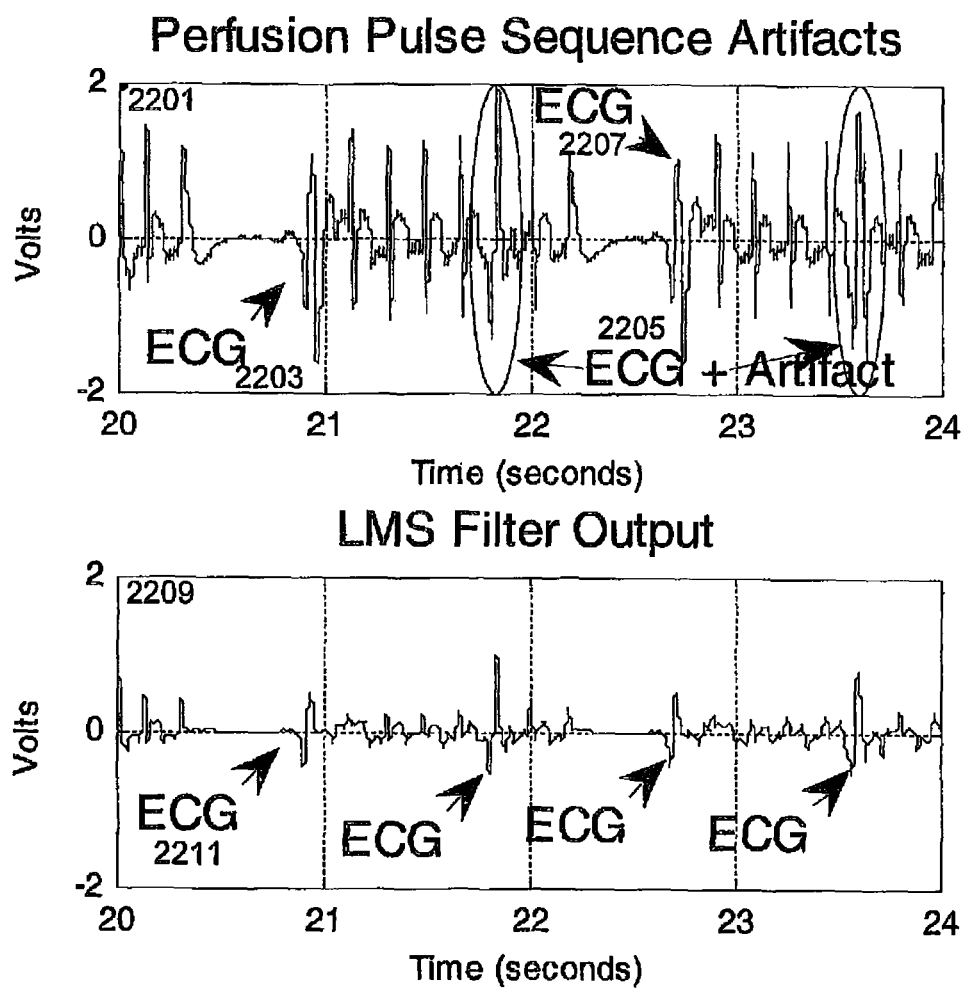
FIG. 34 shows input and output signals of the digital signal processing. The first graph shows ECG data plagued by gradient noise resulting from the Perfusion pulse sequence, while the second chart displays the output from the LMS algorithm. The noise is attenuated to such an extent that the ECG signal is completely visible.

FIG. 4 shows the flowchart of the software signal processing 80 tasks and FIG. 6 shows the flowchart of the implementation of the LMS algorithm 130. The data is sampled at 4098 samples/second 131 at 16 bits per sample. Through a number of carefully controlled studies, it was determined that a desirable noise reference input for the LMS filter is obtained by adding two or three MRI noise channels (N1+N2) 82. The step size parameter of the LMS filter, $\mu$, in the steepest descent algorithm in our detailed implementation 134 is a function of primary signal power and the number of weights used e.g. 32, or 64. The weight is initially set to zero 135. FIG. 34 shows the primary input consisting of the ECG plus gradient artifacts from the perfusion scan (S1), and the output of the LMS filter. By comparing the LMS output to the original data, the considerable improvement in signal-to-noise ratio is clear.

In FIG. 4, each chest signal S1 83, S2, 86 and S3 89 consists of both the ECG and the magnetic gradient induced artifact. One or more separate chest signals are used as the primary signal of the adaptive filtering algorithm after offset removal 84, 87, 90 and low pass filtering in software. The noise reference signal 82 is produced by adding the two signals from the arm (N1+N2), though a third signal (N3) provides greater accuracy. The noise reference signal, in another embodiment, can be obtained from one of the chest ECG signals. The output of the adaptive algorithm 85, 88, 91 is then used to calculate detection statistics using GSO 92. The detection statistics are used to detect ECG based of one or all three adaptive filter outputs 93, and also to calculate the respiration signal 94. The detection and respiration statistics are then sent to the output 95. The LMS adaptive filter algorithm of FIG. 5 and FIG. 6 acts upon a given signal 103 using a known reference noise 101 to generate a desired noise-free output 112. The ECG signal source 102 is a pair or set of pairs of ECG chest electrodes and the noise source 100 is a pair or set of pairs of arm electrodes or ECG chest electrodes with relatively weak ECG signals. It is an adaptive filter 110, changing with the alterations in the sampled signal to maintain a clean output in a dynamic noise environment. As shown in the details of FIG. 5, the algorithm acts upon the input data 103 using the sampled reference 101 and an initial forgetting factor µ. Each noise sample 104, 105, 106, 136 is multiplied by the weight vector 107, 108 and 109 of length T 114 (the filter order) and summed to produce the dot product Y(t) 111, 137 where:

$$Y(t) = \vec{W} \cdot \vec{N} = \sum_{j=1}^{T} W_j \cdot N_j$$

The resulting dot product Y is subtracted from the data sample P 112, producing an error signal Z 113, 138, 140 which is the filtered output data point:

$$Z_i = P_i - Y_i$$

The weight vector is updated 110, 139 by multiplying the data point by the forgetting factor and the noise data point and adding the product to the initial weight:

$$W_{i+1} = W_i + \mu Z_i \vec{N}$$

The values T and µ can be modified to impact the accuracy and complexity of the filter.

FIG. 34 shows the primary input 2201 consisting of the ECG pulse and gradient artifacts 2203, 2205, 2207, and the output of the LMS filter 2209, in which ECG is detectable 2211. Comparing the LMS output to the original data, there is considerable improvement in the signal-to-noise ratio.

Alternative RLS (Non-Lattice) Adaptive Filter Embodiment

Figure 7:
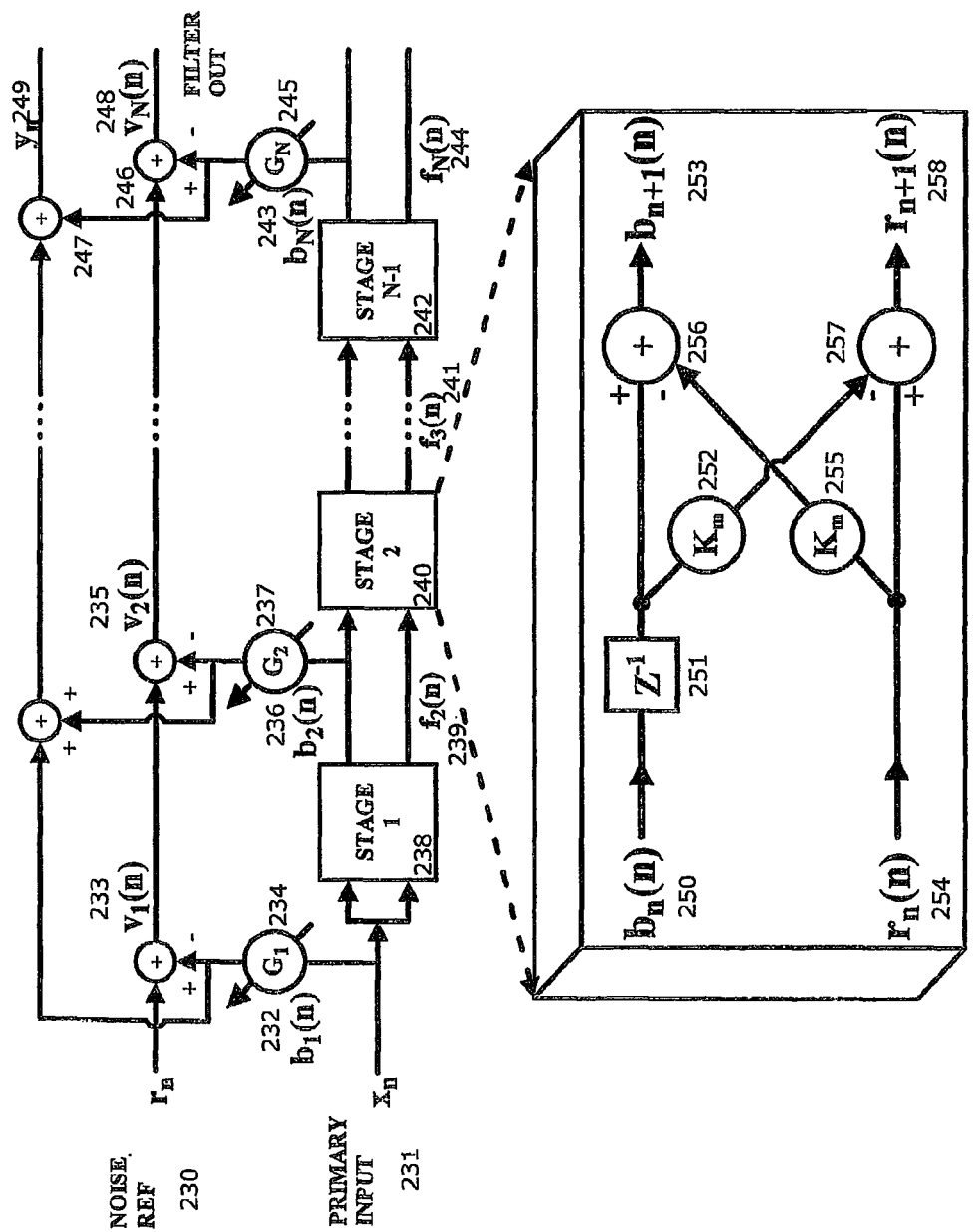
FIG. 7 is a block diagram of a lattice implementation of the RLS adaptive algorithm of FIG. 4.
Figure 8:
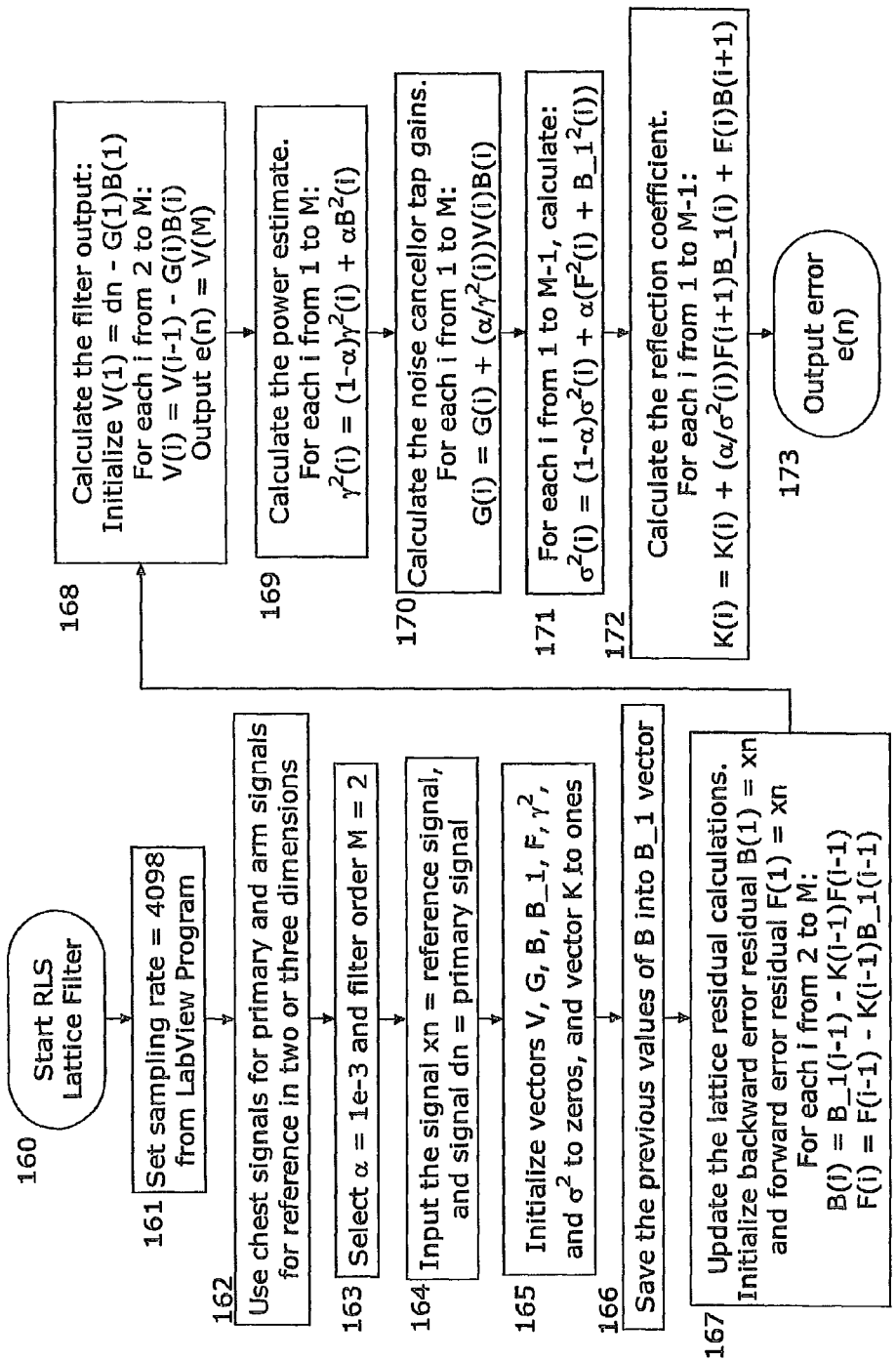
FIG. 8 is a flowchart of a lattice implementation of the RLS adaptive algorithm of FIG. 4.
Figure 9:
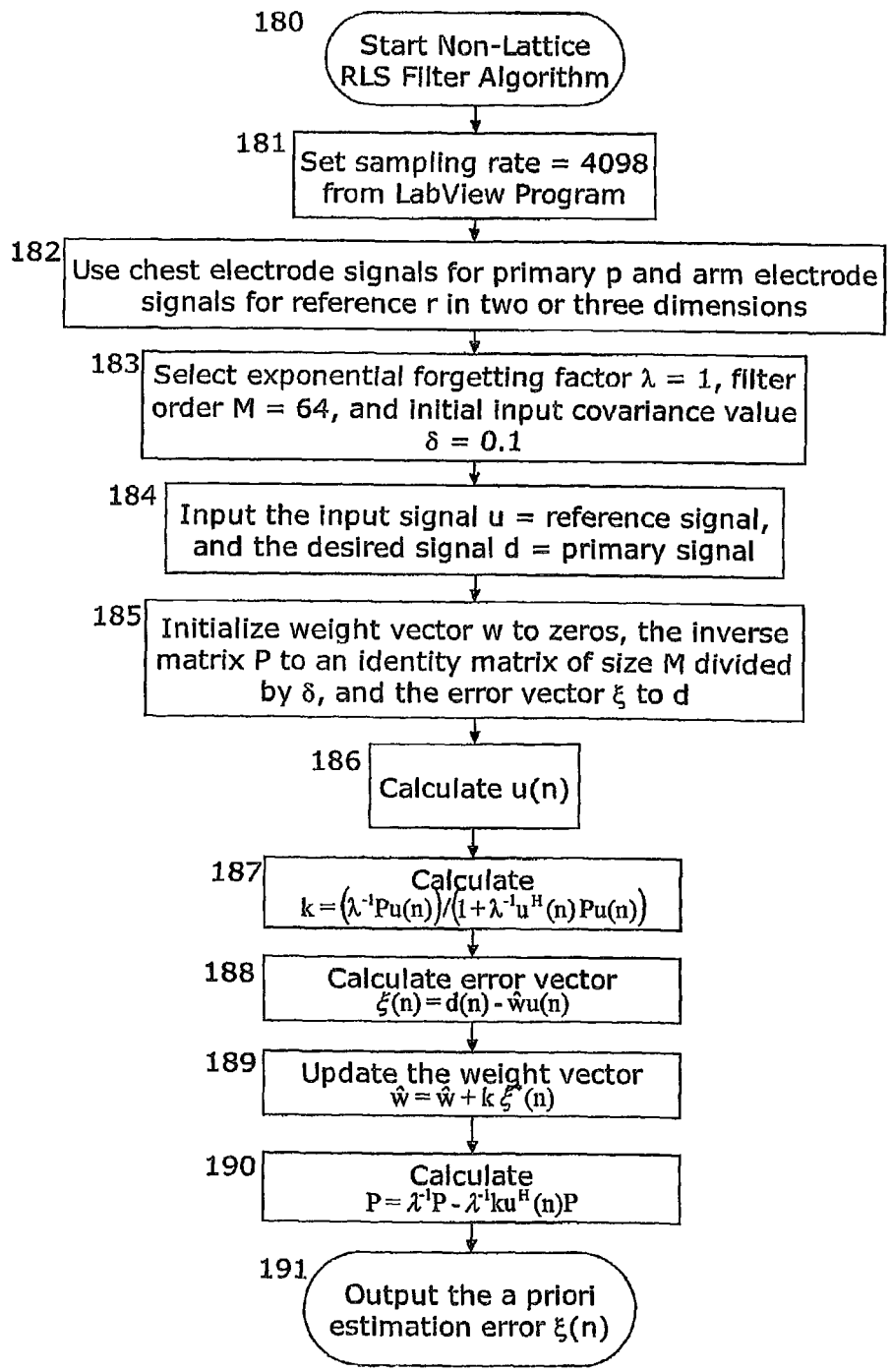
FIG. 9 is a flowchart of the non-lattice implementation of the RLS adaptive algorithm of FIG. 4.

While any adaptive filtering algorithm 85, 88, 91 can be used to remove the noise artifacts from the magnetic gradient ECG signal, alternative embodiments to the LMS to remove either the MDE pulse sequence artifacts or the artifacts from the perfusion pulse sequence may use a lattice implementation FIGS. 7 and 8, or a non-lattice implementation FIG. 9 of the Recursive Least Squares (RLS) algorithms.

Alternative RLS Lattice Adaptive Filter Embodiment

Alternatively the RLS can also be implemented using a lattice structure as diagrammed in FIG. 7. The primary input 231 goes through a sequence of stages 238, 240, 242. Each stage has two outputs: backward error residual 236, 243, 250, 253 and forward error residual 239, 241, 244, 254, 258. The first backward error residual $b_1(n)$ 232 is taken from the primary input 231. In each stage, a lattice is formed consisting of a unit delay 251, reflection coefficients 252, 255 and adders 256, 257. The backward residual errors 232, 236, 243 are multiplied by corresponding gains 234, 237, 245, and subtracted 233, 235, 246 from the noise reference 230, to form the filter output 248 and the power estimate 247, 249. FIG. 8 shows the RLS Lattice 160 flowchart. The sampling rate 161 is set at 4098. Chest electrode signals are used for primary and arm electrode signals are used for reference 162. The value of cc and the filter order M are again chosen to maximize accuracy and minimize processing 163. The primary signal is do and the reference signal is xn 164. The vectors V, G, B, B_1, F, $\gamma^2$, and $\sigma^2$ are initialized to zeros, and vector K is initialized to ones 165. For each instant of time n=1, 2, ... the previous values of B are saved into the vector B_1 166. The lattice residual forward (F) and backward (B) errors are initialized 167:

$$B(n) = F(n) = xn$$

and updated for each i from 2 to M:

$$B(i) = B\_1(i-1) - K(i-1)F(i-1)$$

$$F(i) = F(i-1) - K(i-1)B\_1(i-1)$$

The filter output vector is initialized as 168:

$$V(1) = dn - G(1)B(1)$$

and for each i from 2 to M:

$$V(i) = V(i-1) - G(i)B(i)$$

Where the actual output for time n is:

$$e(n) = V(M)$$

The power estimate is calculated for each i from 1 to M 169:

$$\gamma^2(i) = (1-\alpha)\gamma^2(i) + aB^2(i)$$

and the noise canceller tap gains are calculated for each i from 1 to M 170:

$$G(i) = G(i) + \frac{\alpha}{\gamma^2(i)} V(i)B(i)$$

Then, for each i from 1 to M−1 171:

$$\sigma^2(i) = (1-\alpha)\sigma^2(i) + \alpha(F^2(i) + B\_1^2(i))$$

Finally the reflection coefficient is calculated for each i from 1 to M−1 172:

$$K(i) = K(i) + \frac{\alpha}{\sigma^2(i)} F(i+1)B\_1(i) + F(i)B(i+1)$$

The output of the RLS lattice filter is the error e(n) 173.

In an alternative adaptive algorithm embodiment, the non-lattice RLS filter algorithm 180 of FIG. 9 acts upon the same signal of the LMS using the same known reference noise 182 and samples are the data at 4098 samples/second 181. The exponential forgetting factor λ, filter order M, and initial input covariance value δ 183 are chosen to maximize accuracy and minimize processing. Here, the primary signal is the desired signal d and the reference signal is the input signal u 184. The weight vector w is initialized to zeros, the inverse matrix P to an identity matrix of size M/8, and the error vector to d 185. For each instant of time n=1, 2, . . . the u(n) is calculated 186, and the following are computed 187, 188, 189, 190:

$$k=(\lambda^{-1}Pu(n))/(1+\lambda^{-1}u^H(n)Pu(n))$$

$$\xi(n)=d(n)-\hat{w}u(n)$$

$$\hat{w}=\hat{w}+k\xi^*(n)$$

$$P=\lambda^{-1}P-\lambda^{-1}ku^H(n)P$$

The output of the filter is the a priori estimation error $\xi(n)$ 191.

Recursive Least Squares (RLS) Lattice Adaptive MR Artifact Cancellation Methods

Figure 35:
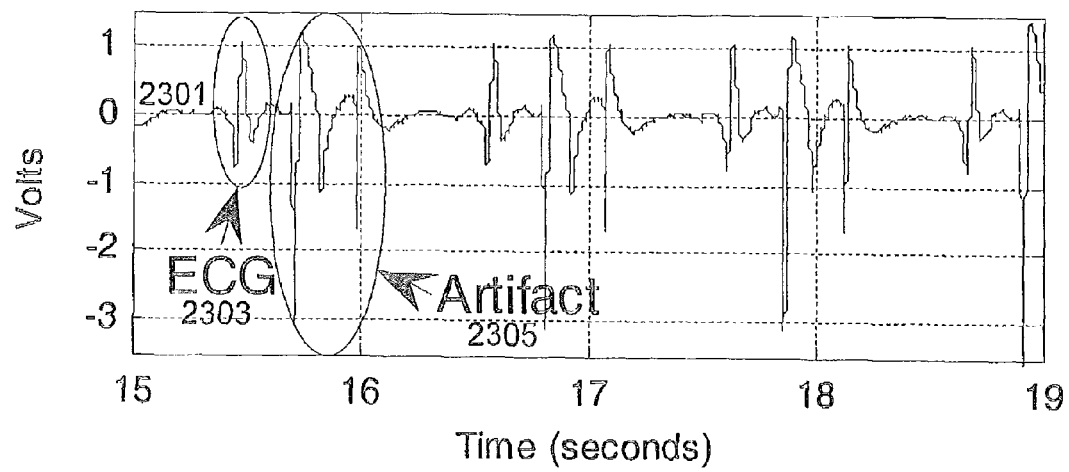
FIG. 35 shows the result of RLS adaptive lattice filtering on the ECG contaminated with artifacts from an MDE MR gradient sequence.
Figure 35:
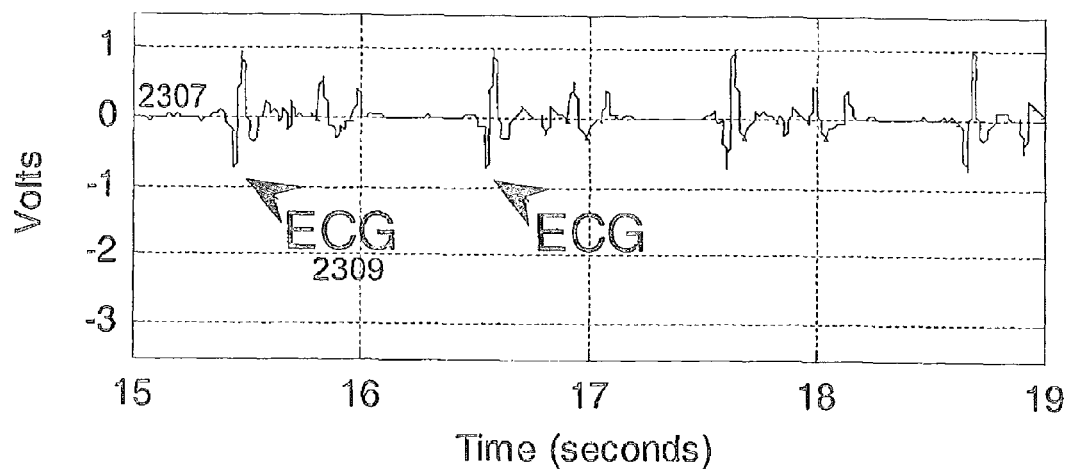

One result achieved using the RLS adaptive lattice noise cancellation filter is shown in FIG. 35. The "primary" input 2301 to the lattice filter is the ECG 2303 contaminated with artifacts 2305 from an MDE MR gradient sequence as shown unprocessed at the top of FIG. 35. Note the small amplitude of the ECG compared to the larger amplitude of the MDE gradient artifact. The output of the adaptive lattice filter is shown in the bottom tracing 2307 of FIG. 35. This tracing shows that the amplitude of the ECG 2309 remains virtually unchanged while the gradient artifact noise is markedly reduced, making subsequent R-wave detection possible.

GSO ECG Vector Framework Method for Detection

Figure 10:
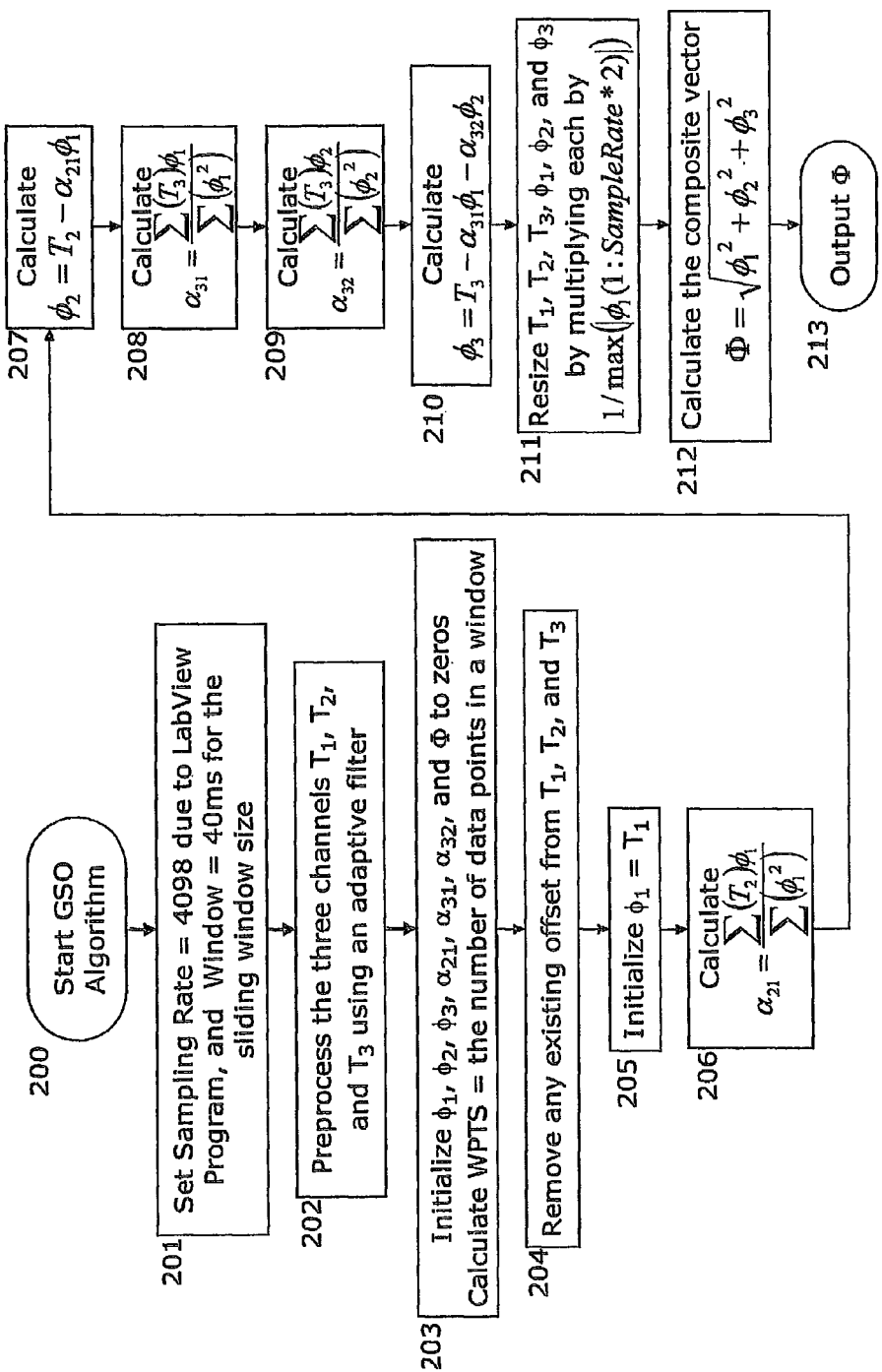
FIG. 10 is a flowchart of the GSO vectorization of FIG. 4.

Following the effective cancellation of the RF and magnetic gradient artifacts using one of the adaptive noise cancellation methods, the next step in the MRI ECG digital signal processing methods is to construct the Gram-Schmidt Orthogonalization (GSO) vector signal set used for ultimate ECG detection. FIG. 10 shows the flowchart of the GSO algorithm 200. The GSO ECG vector concept and approach entails transforming a set of ECG thoracic leads (or signals), using the GSO process, into an orthogonal ECG basis set of vectors. The approach does not require critical electrode placement, since the GSO ECG vectors are computed exactly and are not calculated a priori.

The algorithm to obtain the GSO "optimum vector signal set" can be implemented in software using MATLAB. The two or three ECG signals (S1, S2 and S3) are collected from the left upper chest in the frontal, sagittal, and coronal planes of the body. These are the X-Z, Z-Y, and X-Y planes of the MR magnet bore, respectively.

The ECG data is acquired at a sampling rate of 4098, and the GSO window is 40 ms 201. When the ECG data is acquired within the magnet, it is subjected to the MR magnetic gradient artifacts. Therefore, only after the effective cancellation of these artifacts by the adaptive noise cancellation process can the thoracic ECG signals T, T2, and T3 202 be combined and used to provide an optimum GSO vector for subsequent ECG detection. The GSO vector set completely describes the intrinsic temporal and spatial components of the ECG signal, and provides the R-wave's maximum composite amplitude and maximum slope for optimal detection via the derivative.

Figure 12:
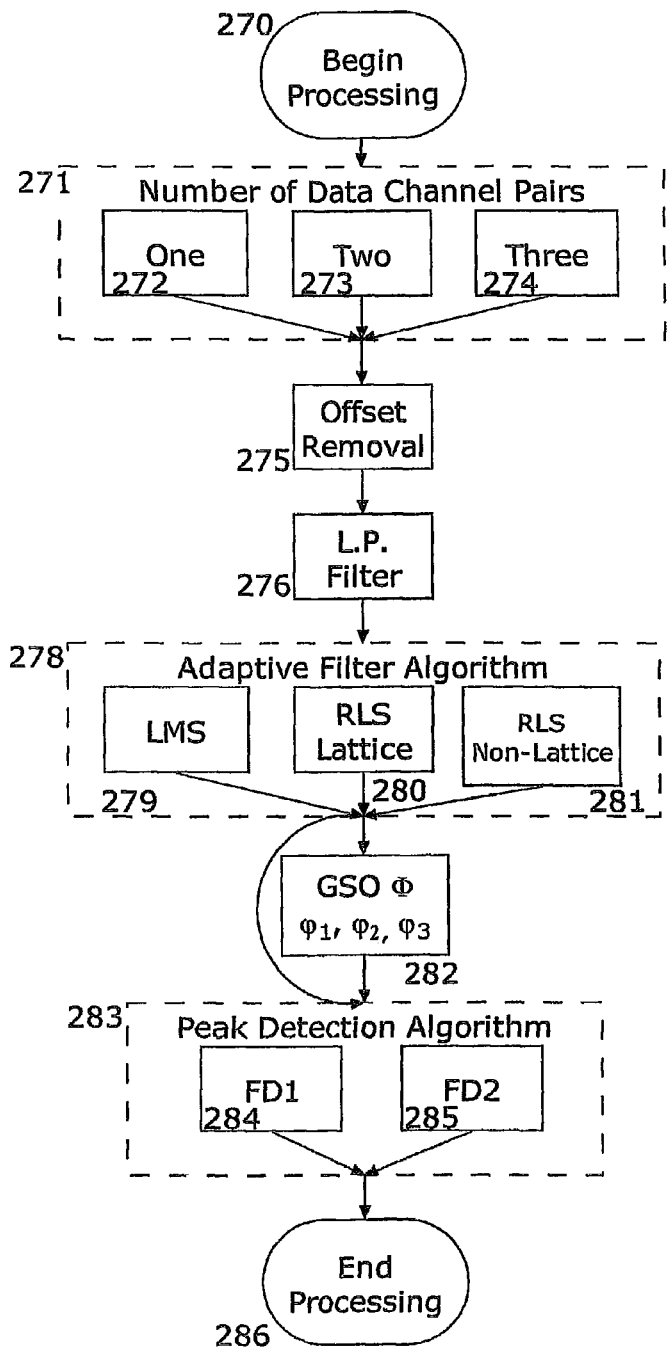
FIG. 12 is a flowchart showing the possible execution paths for one, two, or three channels of ECG data through one of three adaptive filtering algorithms, with or without GSO vectorization, and one of two derivative detection algorithms.
Figure 13:
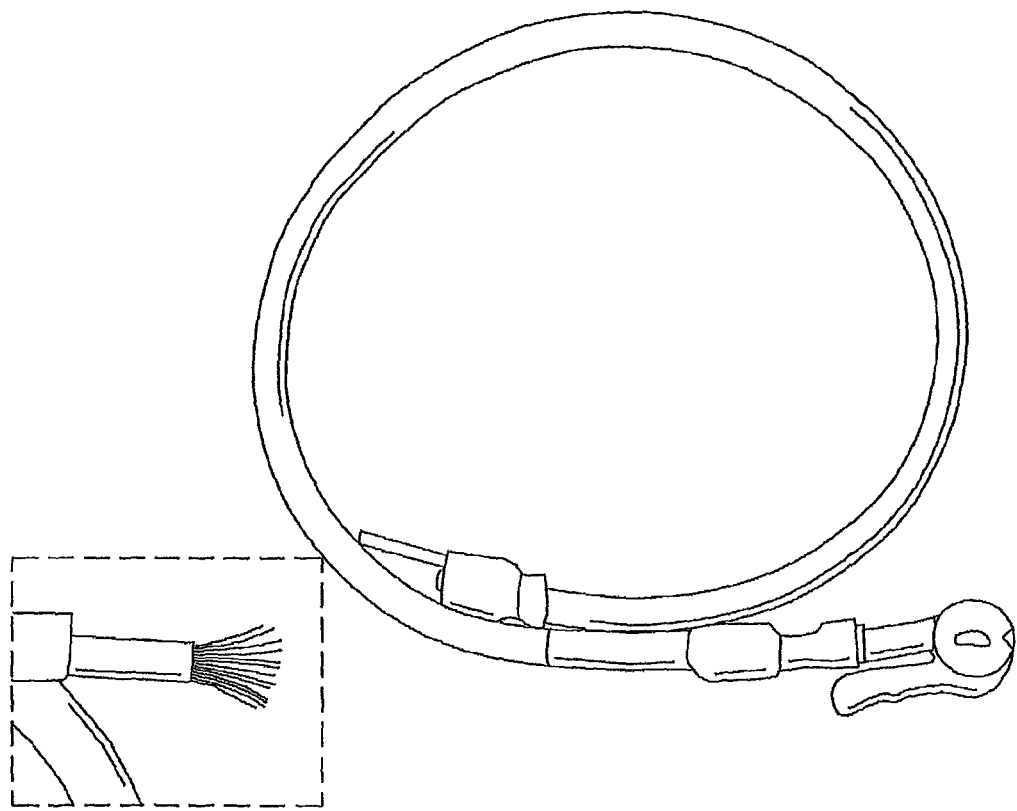
FIG. 13 is a photograph of the MRI compatible ECG lead wire, showing the ECG electrode clip and non-ferrous connector. The inset details the non-metallic, high-resistance carbon filament fiber coated with conductive acrylic latex.

After having adaptively filtered each chest signal (S1, S2, and S3) separately, the results (T1, T2, and T3) can be combined into a single three-dimensional detection statistic Φ 211, 212 using the Gram-Schmidt Orthogonalization (GSO) algorithm as shown in FIG. 4 item 92 and FIG. 12 item 282, and detailed in FIG. 10 with the following set of equations initialized at zero 203:

$$\phi_1(t)=T_1(t)-T_{1av}\,204,205,210$$

$$\phi_2(t)=T_2(t)-\alpha_{21}*\phi_1(t)-T_{2av}\,204,207,210$$

$$\phi_3(t)=T_3(t)-\alpha_{31}*\phi_1(t)-\alpha_{32}*(t)-T_{3av}\,204,210$$

$$\Phi=\sqrt{\phi_1^2+\phi_2^2+\phi_3^2}\,212$$

where:

$\alpha_{ij}=\Sigma[T_i(t)-T_{iav}]*\phi_j(t)/\tau[\phi_j^2(t)]$, and 206, 208, 209

$T_{iav}$=the average dc value of $T_i$.

The filtered three-dimensional ECG detection statistic Φ 213 can be processed through an R-wave detection algorithm such as one based on the first derivative.

Respiration Determination Method by GSO Vector Coefficients

The GSO vector set represents the intrinsic components of the ECG as a function of time and space. These components change as a function of respiration. From a physiologic point of view, as the diaphragm moves, the lungs and the heart change the direction of the electrocardiogram QRS complex cardiac dipole and the coefficients change. Thus there is an indirect means of monitoring respiration utilizing the ECG without the need for a separate respiratory sensor and its signal conditioning electrical interface.

As the heart is rotated by the diaphragm during breathing, it presents a different projection on the body surface, depending on the relative position of the heart within the chest. In addition, the cyclic behavior of these coefficients is also due to the changing thoracic resistivity caused by air in the lungs and the alterations in thoracic geometry and lung vasculature.

This approach is utilized to develop an indicator of respiration from the ECG GSO vector coefficients. Two ($T_1$ and $T_2$) or three ($T_1$, $T_2$, and $T_3$) ECG signal vectors are used, which are collected from the subject's chest using a common reference according to the ECG lead configuration previously described. One subject was instructed to inhale and exhale at five second intervals using a stopwatch to produce a respiration rate of 0.1 Hz. MATLAB was used to compute and plot one of the GSO coefficients.

Figure 29:
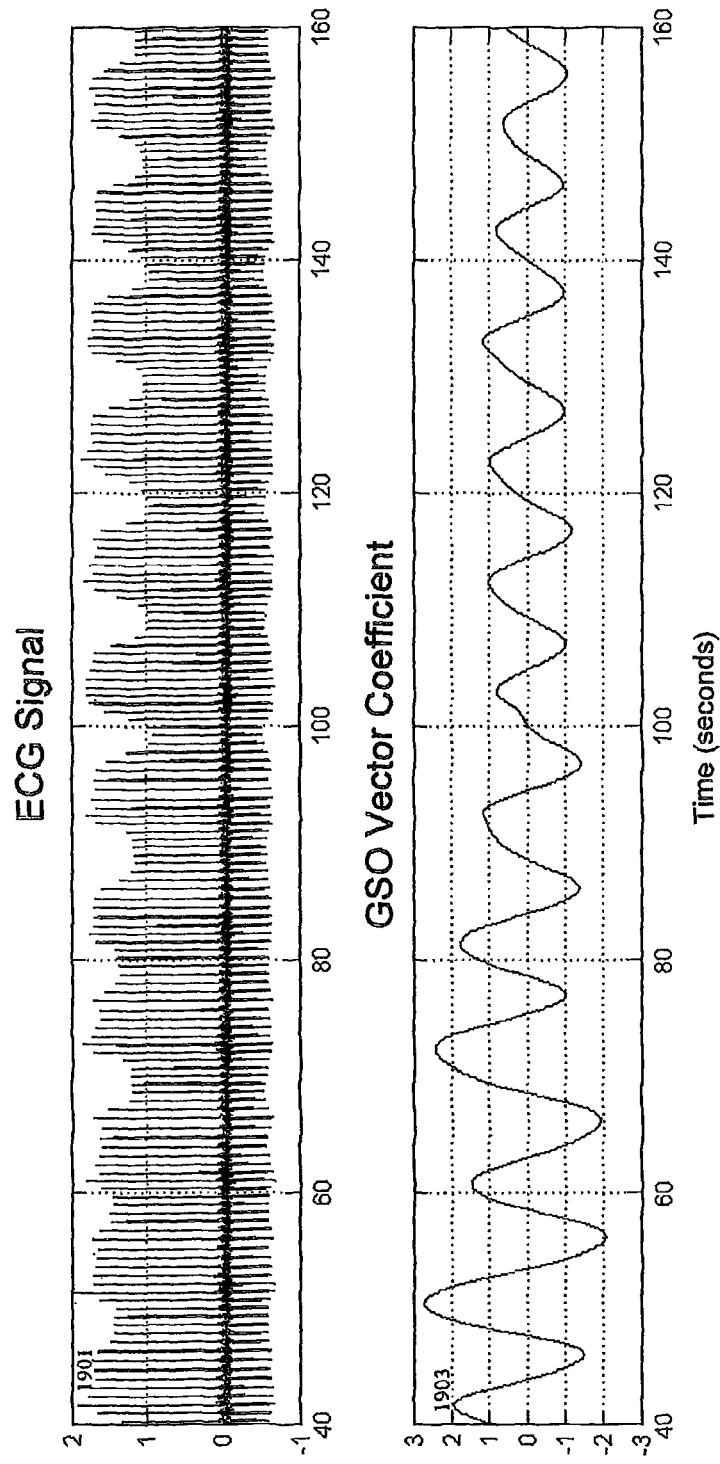
FIG. 29 shows the well known time-varying amplitude variations of the ECG signal, with breathing, are reflected in the oscillations of the GSO vector coefficient. We propose to use the GSO vector coefficients as a measure of respiration, and thus not require a separate transducer and electronics to monitor breathing.

FIG. 29 illustrates the cyclic time-variation in this GSO vector coefficient 1903. The time varying R-Wave peak amplitudes of the recorded $T_1$ ECG signal 1901 is shown over the course of 120 seconds reflecting the subject's respiratory rate. The GSO algorithm produced a time-varying coefficient which reflects this respiration. This is illustrated in FIG. 29 after the time-varying coefficient passing through a bandpass filter at 0.03 and 0.2 Hz. The cyclic variation in this coefficient clearly illustrates the quality of this derived respiration signal.

MRI ECG Derivative Detection Methods

Figure 11:
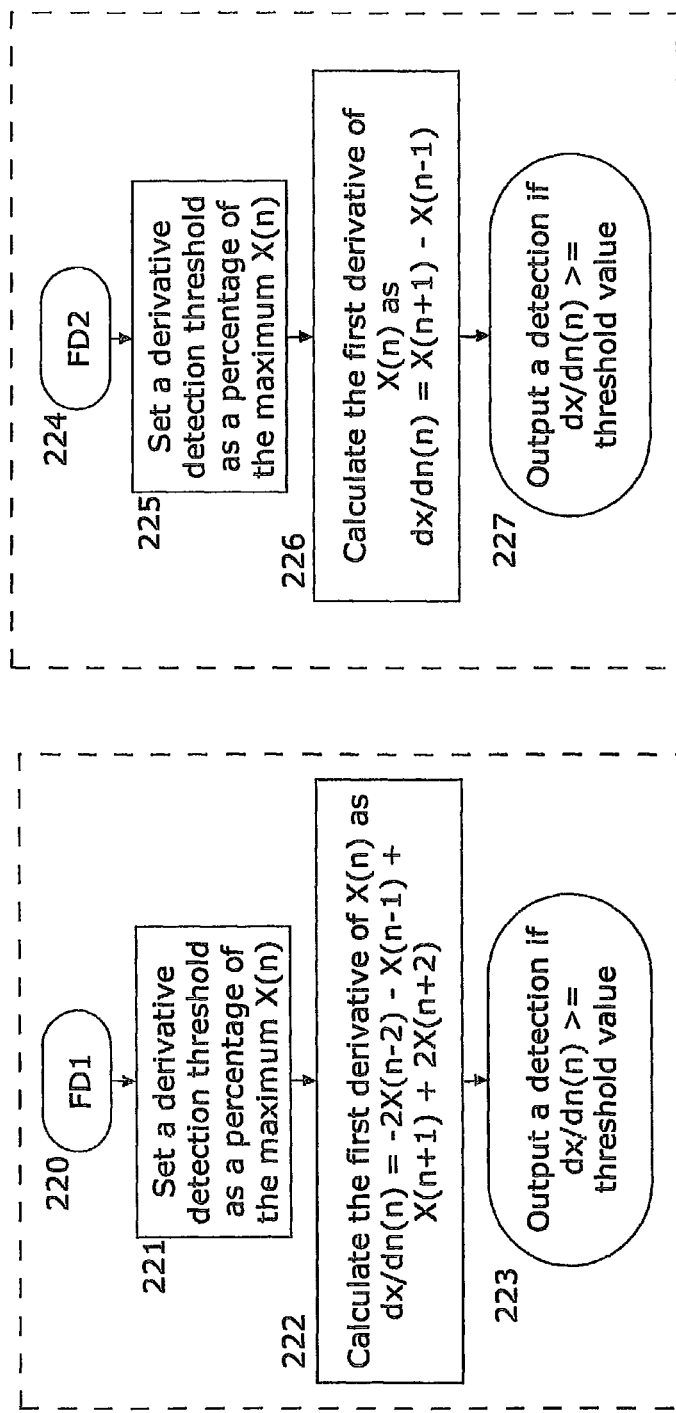
FIG. 11 is a flowchart of two first derivative detection algorithms of FIG. 4.

The derivative detection approach to detect the ECG signal is based on a threshold crossing of the first digital derivative of the ECG R-wave. Two derivative approaches are shown in FIG. 11. They are designate here as "FD1" 220 and "FD2" 224. The effectiveness of each derivative approach is evaluated.

The first method FD1 is given by 222:

$$Y(n)=-2X(n-2)-X(n-1)+X(n+1)+2X(n+2), 2<n<N-2$$

where N is the number of data points, X(n) is the composite GSO vector, and Y(n) is the computed first derivative. The second method FD2 is given by 226:

$$Y(n)=X(n+1)-X(n-1), 2<n<N-1$$

where N is the number of points, X(n) is the filtered ECG data, and Y(n) is the computed first derivative.

After computing the first derivatives, according to FD1 and FD2, the detection of an R-wave is declared each time that the first derivative exceeds a predetermined threshold value 221 and 223 for FD1 and 225 and 227 for FD2. The threshold values can be chosen to yield virtually 100% detection of the R-waves collected from normal subjects.

Signal Flow Overview

FIG. 12 illustrates that there are several combinations of signal processing steps 270 that can be utilized to provide an optimal detection of ECG signals within MRI gradient artifacts and RF noise.

First, one, 272 two, 273 or three 274 ECG signals 271 can be used to formulate the optimum ECG vector for detection. Similarly, one, two or three noise reference signals can be obtained from the arm. Alternatively, if signals are collected only from the chest, those signals that contain a weak ECG signal can be used for the noise reference signals. In this case, only one ECG signal and one noise reference signal will be collected. Following the data collection, any DC voltage offset will be removed from all inputs 275 and each input will be passed through a low pass filter 276. The next step in the processing is to select a particular adaptive algorithm 278 to remove gradient artifacts for each particular sequence. The LMS 279 adaptive algorithm is the simplest algorithm to use for all pulse sequences. Alternative adaptive algorithms to remove the gradient artifact noise include the RLS lattice algorithm 280 and the RLS non-lattice algorithm 281. Following removal of the gradient artifacts by adaptive filtering, the various ECG signals which may include one, two or three signals may be combined into one vector statistic for detection using the GSO 282 algorithm. The use of this GSO vector processing technique is optional in order to provide for optimal detection. Finally, detection of the ECG is accomplished by the use of one or more derivative detection algorithms 283. The two derivative techniques are based on a digital derivative method referred to as FD1 284 and FD2 285. Detection is accomplished by the use of either FD1 or FD2 or a combination of the two and this completes processing 286 to provide a trigger signal to initiate the MR magnetic gradient pulse sequence and RF pulses.

Figure 17:
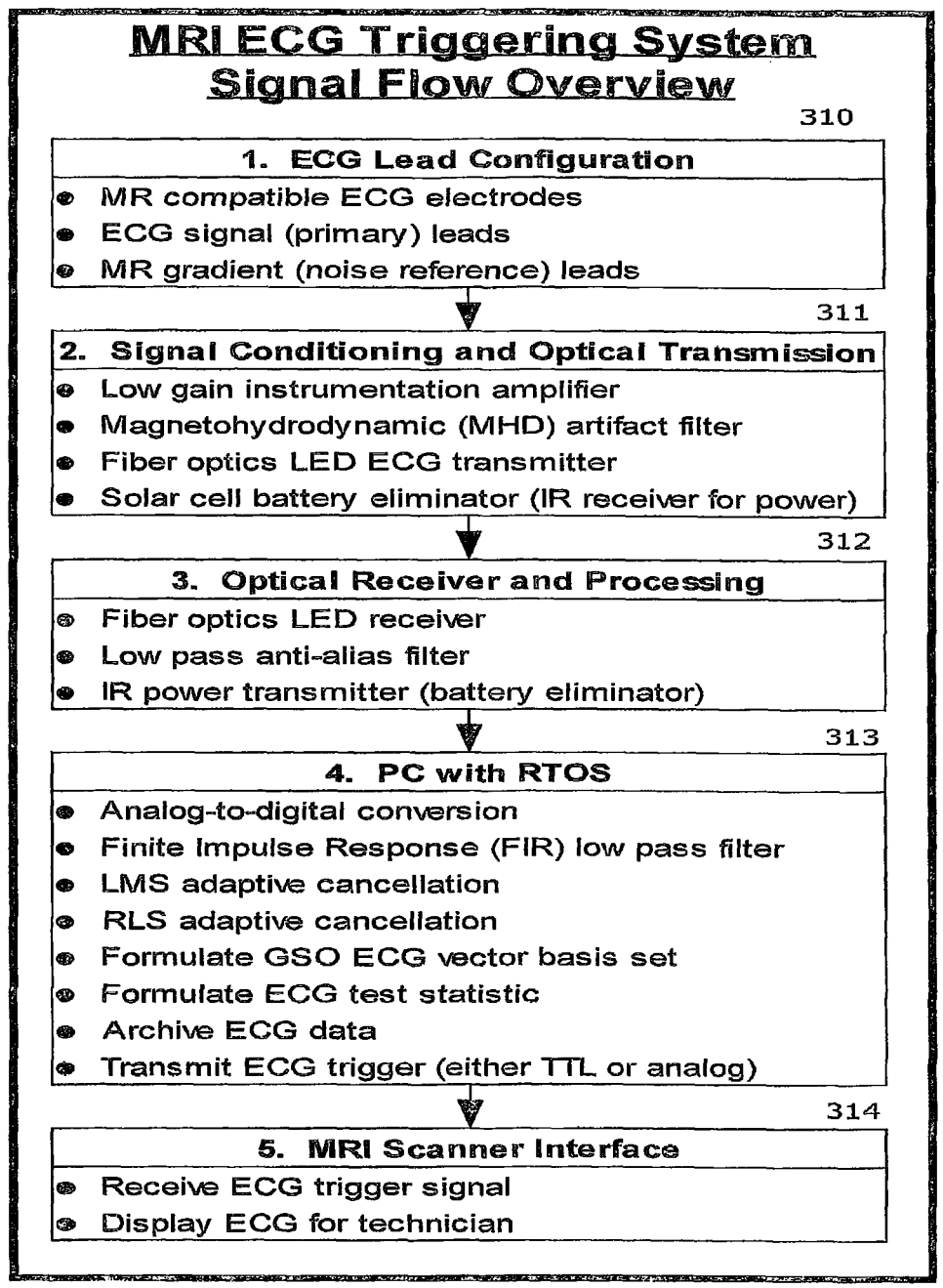
FIG. 17 is an overview of the complete analog and digital signal processing of the ECG trigger system.

FIG. 17 provides a comprehensive signal flow overview of the entire MRI ECG triggering system. Step One is an ECG Lead Configuration 310 consisting of up to 3 ECG signals and three noise signals which are acquired to minimize false positive and false negative detections. Step Two is Signal Conditioning and Optical Transmission 311 which provides for low gain amplification, a magnetohydrodynamic (MHD) artifact filter, a fiber optic LED ECG transmitter, and may also include a solar cell battery eliminator. Step Three is Optical Receiver and Processing 312 consisting of an LED optical receiver for receiving the ECG signals either through the air or fiber optics, a low pass anti-alias filter and an IR power supply which may also include a battery eliminator. Step Four consists of a Personal Computer with a Real-Time Operating System (RTOS) 313 which performs the digital signal processing. A Hamming weighted Finite Impulse Response (FIR) low pass digital filter attenuates gradient artifacts in excess of 30 Hz and moderate Gibbs Phenomena processing artifacts. The fast Fourier transform (FFT) approach, which may be too computationally intensive for real-time implementation, is an alternative to the FIR filter. The LMS adaptive noise canceller uses various numbers of weights, one filter structure for each of the x, y, and z gradient artifacts or a single filter structure with a single noise reference as the sum of the gradient artifacts. The RLS is an alternative adaptive noise canceller and has advantages compared with the LMS algorithm, including: faster convergence, greater stability, and fewer filter weights compared with its more complex operations. Step Five consists of the MRI Scanner Interface 314 which consists of transmitting an electrical signal to cause the MRI scanner to emit a pulse sequence and a display of the ECG signal for the MRI technician.

Figure 30:
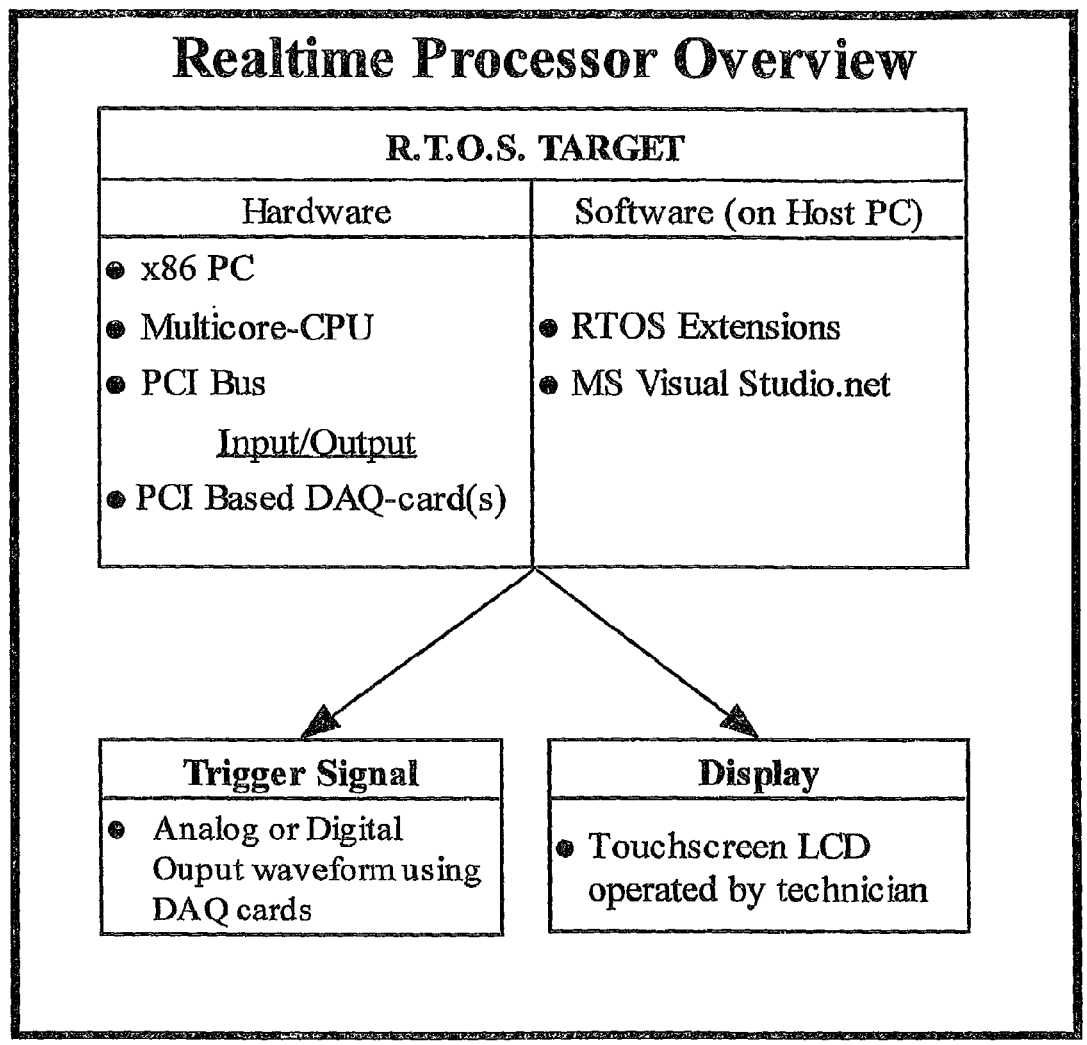
FIG. 30 shows an overview of the MRI ECG triggering system as a real-time embedded computer system.

The embedded computer real-time operating system (RTOS) provides the ECG trigger to the scanner in a timely fashion. An overview of the MRI ECG triggering system as a real-time embedded computer system is shown in FIG. 30. The figure provides a block diagram of the hardware and software of the RTOS target computer and host computer development system._The MATLAB software modules that execute the FIR, LMS and RLS adaptive noise cancellation and other signal processing algorithms are optimized for performance. These MATLAB modules are modified and represented in fixed-point arithmetic to assure the most rapid execution of these mathematically intense software modules within a RTOS. These fixed-point algorithms are rewritten from MATLAB code into C/C++-code, as needed, to provide a compatible format for the RTOS compiler. The IDE runs on an x86 multicore PC which serves as the "host" machine. Finally, the optimized code is downloaded to the target system for execution in real-time and a digital pulse representing the ECG trigger signal is interfaced with the MR scanner to initiate the RF and magnetic gradient pulse sequences. This target system is simply another x86 multicore PC.

Figure 31:
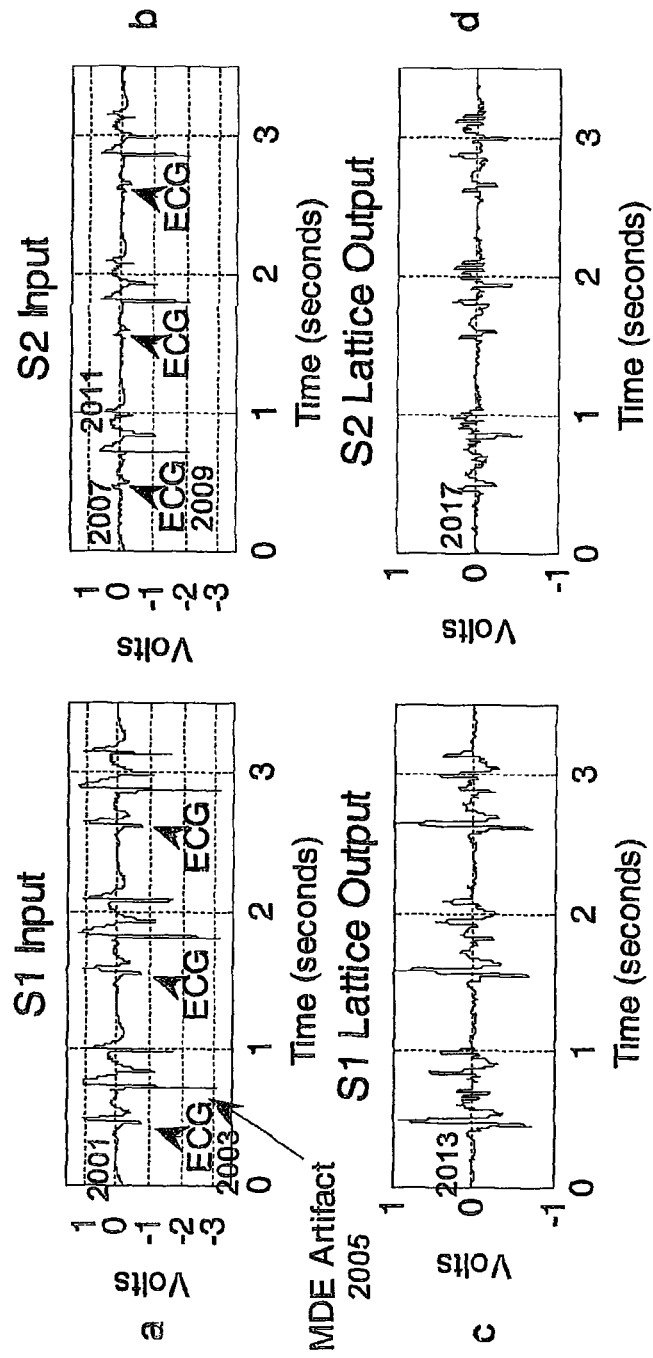
FIG. 31 shows first derivative detection effectiveness: (a) MDE S1 channel before digital processing; (b) MDE S2 channel before digital processing; (c) MDE S1 channel after FFT filtering and adaptive RLS filtering; (d) MDE S2 channel after FFT filtering and adaptive RLS filtering; (e) Sum of processed S1 and S2 signals with peak detections; (f) FD1 derivative with peak detections; (g) Magnification of first ECG peak showing the start of the R-wave and the FD1 detection point.
Figure 31:
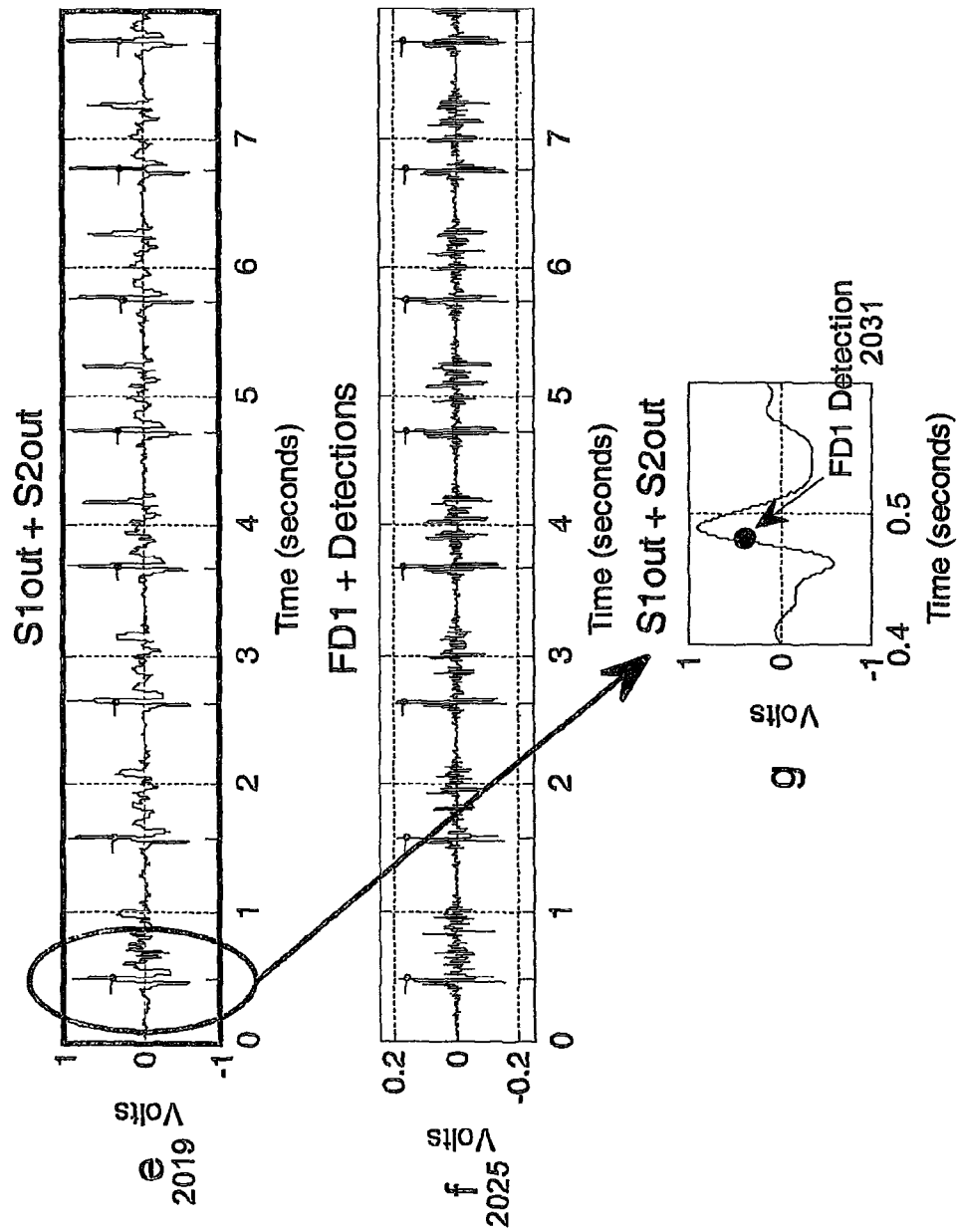

FIG. 31 summarizes the digital signal processing. The first 3½ seconds of the unprocessed thoracic ECG data S1 (a) 2001 and S2 (b) 2007, containing the ECG plus 2003, 2009 myocardial delayed enhancement (MDE) MR pulse sequence gradient artifacts 2005, 2011 are shown. Those signals are low-pass filtered at 30 Hz, using the hamming weighted finite impulse response digital filter, and then adaptively filtered using the RLS lattice filter with noise channels (N1+N2) as the noise reference for each of two lattice channels. The respective adaptive lattice outputs are shown in (c) 2013 and (d) 2017 with the amplitude of the signal relative to the noise greatly improved due to the digital filtering. The two outputs of the lattice filter are then combined into one ECG signal vector (e) 2019 using the GSO algorithm, and used as the test statistic for first derivative R-wave detection.

The first derivative of the GSO vector is computed using the FD1 algorithm, and shown in (f) 2025. Also shown are vertical ticks, marking the time at which the ECGs are detected 2023, 2029, and horizontal flags, marking the amplitude of the corresponding test statistic at the corresponding time of the declared detection 2021, 2027, 2031. All eight ECGs are detected on the rising edge of the R-wave as shown in the magnified ECG at the bottom of the figure (g). For the very limited eight second subset of the data, no false positives, due to the MR gradient noise, or false negatives, from an ECG derivative not reaching the set threshold value occurred.

Battery Eliminator

Figure 16:
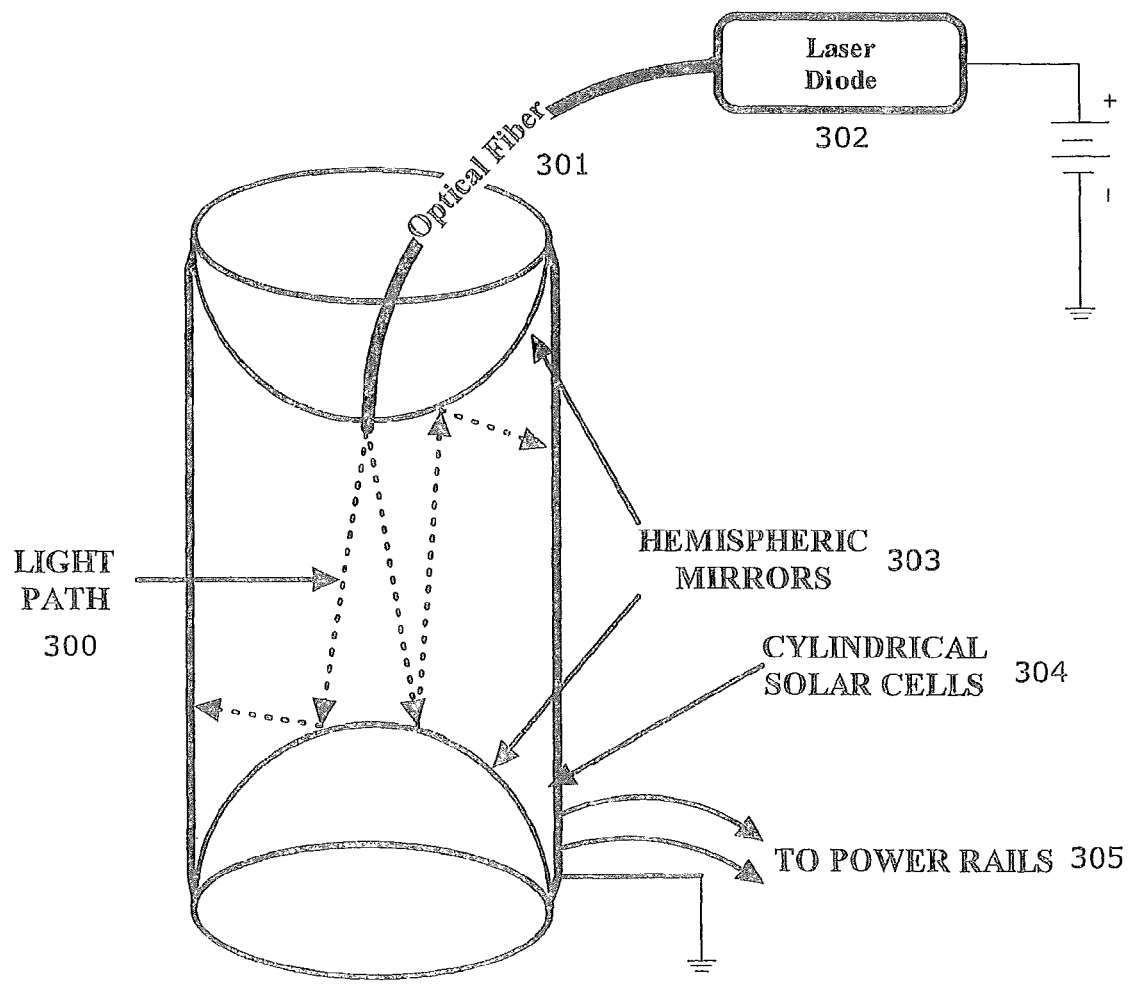
FIG. 16 is a schematic diagram of the battery eliminator. A 2.2 W 808 nm laser diode and optical fiber is used to pipe in light to a solar cell, which is configured in a cylinder, producing 3.3 volts and power the ECG amplifier.

In an alternative embodiment, the batteries within the optical transmitter are replaced with a battery eliminator. FIG. 16 illustrates the "battery eliminator" which is fabricated from flexible solar cell material into the shape of a cylinder. The ends of the cylinder are plugged with two hemispheric minors 303. A plastic optical fiber 301 is led through a hole in one minor and cemented in place. The other end of the fiber is optically coupled to a medium power (<2 W) laser diode 302. All of the light 300 which is not absorbed by the minors themselves is absorbed by the cylindrical solar cell 304. A 2"×2.5" cylinder of a silicon thin film solar cell produces 3.3V with a 70 mA load when illuminated by a 2.2 W, 808 nm laser diode. Power is transmitted from the battery eliminator to the transmitter power rails 305 via wires.

Other simple designs can be used as well. For example, the inside of the transmitter enclosure can be lined with the photocell material and an optical dispersing element couples to the incoming fiber. Finally, the power is transmitted via an optical fiber from a laser diode, as shown in the figure.

All of the components required for this power system are inexpensive and readily available. Laser diodes can be used from DVD burners, for example. 4 W laser diodes have dropped in price below the $100 level (Spectra Diode Labs SDL 2300 series). Amplifier chips for the ECG transmitter are available in the 1.8-3V<1 mW range (e.g., Texas Instruments OPA379). Virtually all the power draw in the transmitter is due to the LEDs. These LEDs are available with very low threshold current so that total power consumption for a 6 channel transmitter can be kept below 25 mW. Solar cell units can be obtained from numerous vendors and the cost of this aspect of the power transmission is in engineering the light dispersion coupling from the fiber, not the materials themselves. The overall cost of such a power unit is modest considering the lifetime cost of replacement MRI compatible batteries. There are only two or three battery types that can be used in the MRI environment. These batteries are difficult to procure, have a limited shelf-life and cost about $7 apiece.

Wireless Infrared (IR) Transmitter

Figure 18:
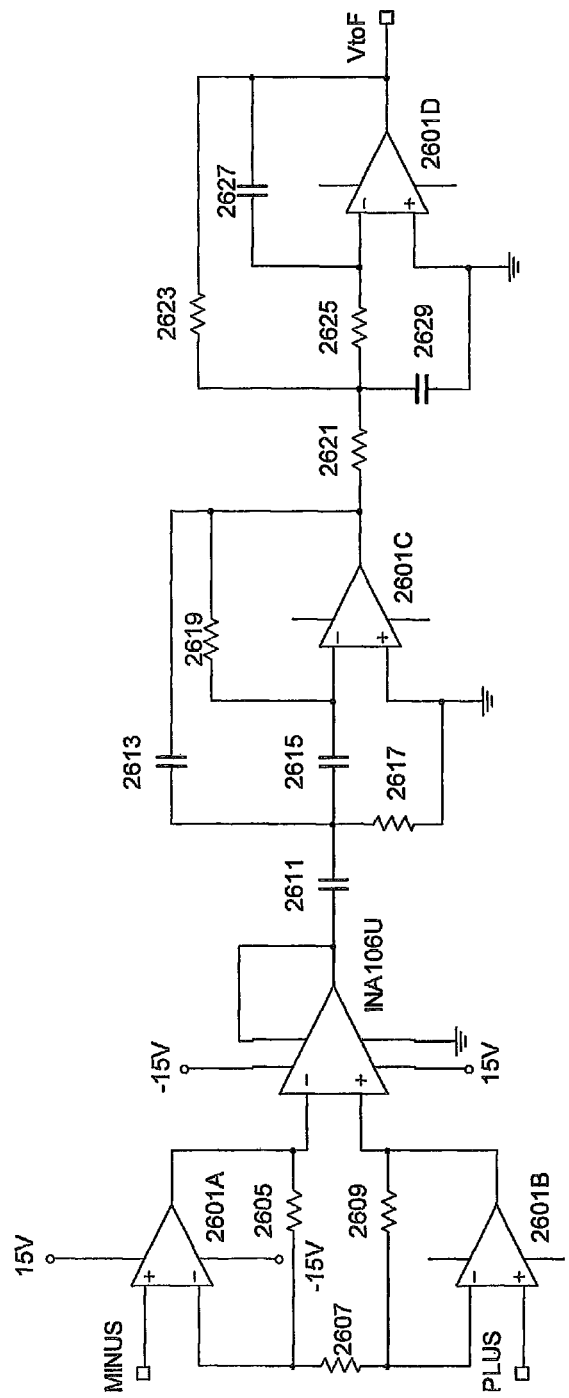
FIG. 18 is an electronic schematic diagram of the prototype ECG amplifier. Refinements and other chip models will allow the circuit to be implemented using only two surface-mount chips.

In another embodiment, shown in FIG. 18, the wireless ECG amplifier is a straight-forward instrumentation amplifier design consisting of op amps 2601A-B and 2603 and gain setting resistors 2605, 2607 and 2609 followed by a conventional high pass filter with op amp 2601C and RC combinations of 2611, 2613, 2615, 2617, 2619 and low pass filter with op amp 2601D and RC combinations of 2621, 2623, 2625, 2627 and 2629. In the circuit shown in FIG. 18 resistor 2607 is used to set the overall gain. Alternatively, the ECG gain may be set by an automatic gain circuit (AGC) to accommodate very low amplitude ECG signals that are frequently seen in patients with heart disease.

In one embodiment, the high-pass filter is set in the range of 1 to 5 Hz, primarily to reduce baseline shifts and electrode artifacts. Filter cutoff frequency is variable in hardware using dip-switches to enhance R-wave detection and allow passage of diagnostic quality ECGs. The low-pass filter is set in the range of 35 to 200 Hz, consistent with standard practice for monitoring or diagnostic ECG.

Figure 19:
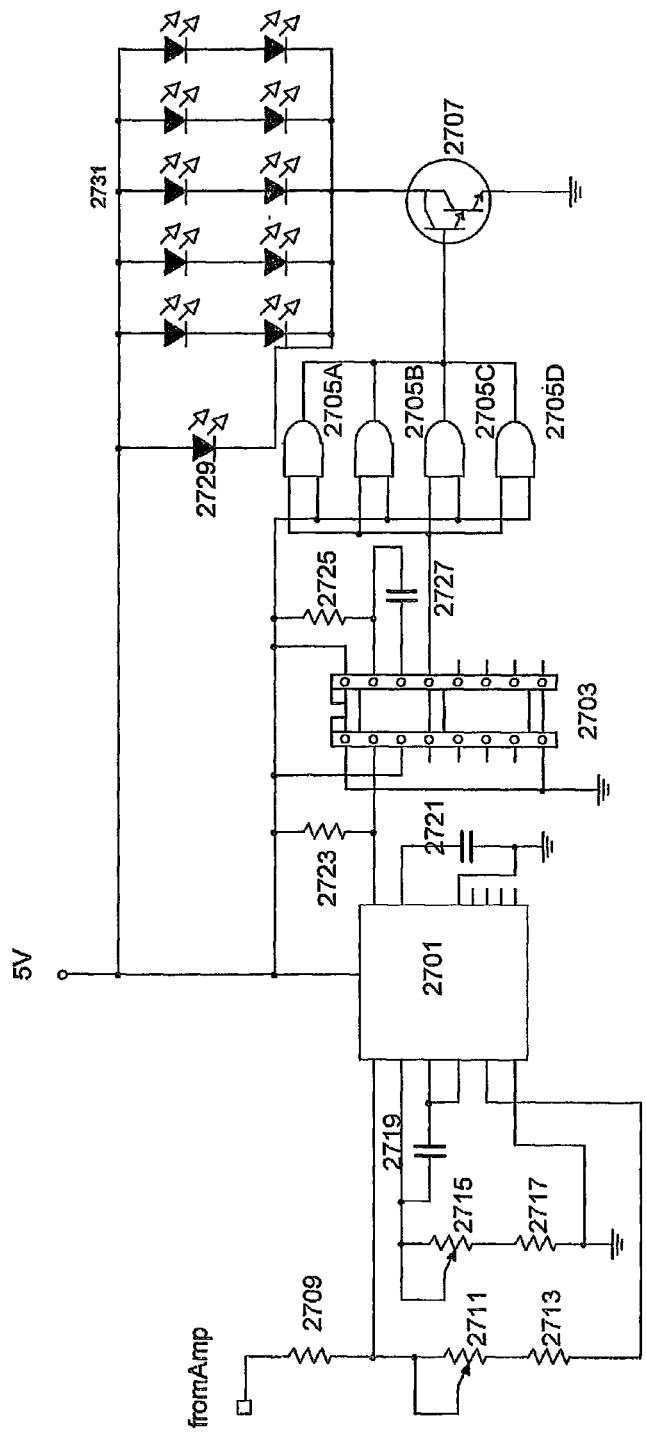
FIG. 19 is an electronic schematic diagram of the prototype IR transmitter. The red LED on the far right is used as a visual indicator that the system is working properly.

In one embodiment, the ECG amplifier output is led to the input of the infrared (IR) transmitter illustrated in FIG. 19, consisting of a voltage-to-frequency (V-F) converter 2701, followed by digital logic and IR LED transmitter 2731 and an on/off indicator LED 2729. The V-F converter 2701 (Burr-Brown VFC121) with supporting components 2709, 2713, 2717, 2719, 2721, 2723 converts ECG analog voltages to frequencies, weighted by potentiometers "ZERO" 2711 and "FULL SCALE" 2715. These are set so that a 1 volt signal is represented by 100 KHz. The output of the V-F converter 2701 is shaped by a Schmitt trigger one shot 2703 (74HCT221), with supporting components 2725 and 2727.

The standardized 1 µS pulses produced by the one-shot are led to AND gates 2705A-D, solely to increase the current drive for the light emitting diode (LED) switching transistor 2707 (2N6427). The quad 74AHCT08 2705 A-D is connected so that all sections are in parallel, providing the current boost to the transistor. The switching transistor activates the IR LED array 2731. This series-parallel configuration is arranged to maximize the transmitter light output. LED array 2731 is chosen based on the MR imaging site.

In this embodiment, the ECG amplifier, filters, and LED transmitter are housed in a cigarette sized container placed directly on the subject's chest, within approximately 6 inches of the heart. The LED array is on the outside of this package to emit pulses in an omni-directional field with sufficient intensity to be detected by the receiving photodiode mounted outside the MRI room. Direct line of sight between transmitter and receiver is not required. IR reflective material may be placed in the magnet room to allow a strong reflected IR beam to be robustly transmitted to the receiver outside the room.

Wireless Infrared (IR) Receiver

Figure 23:
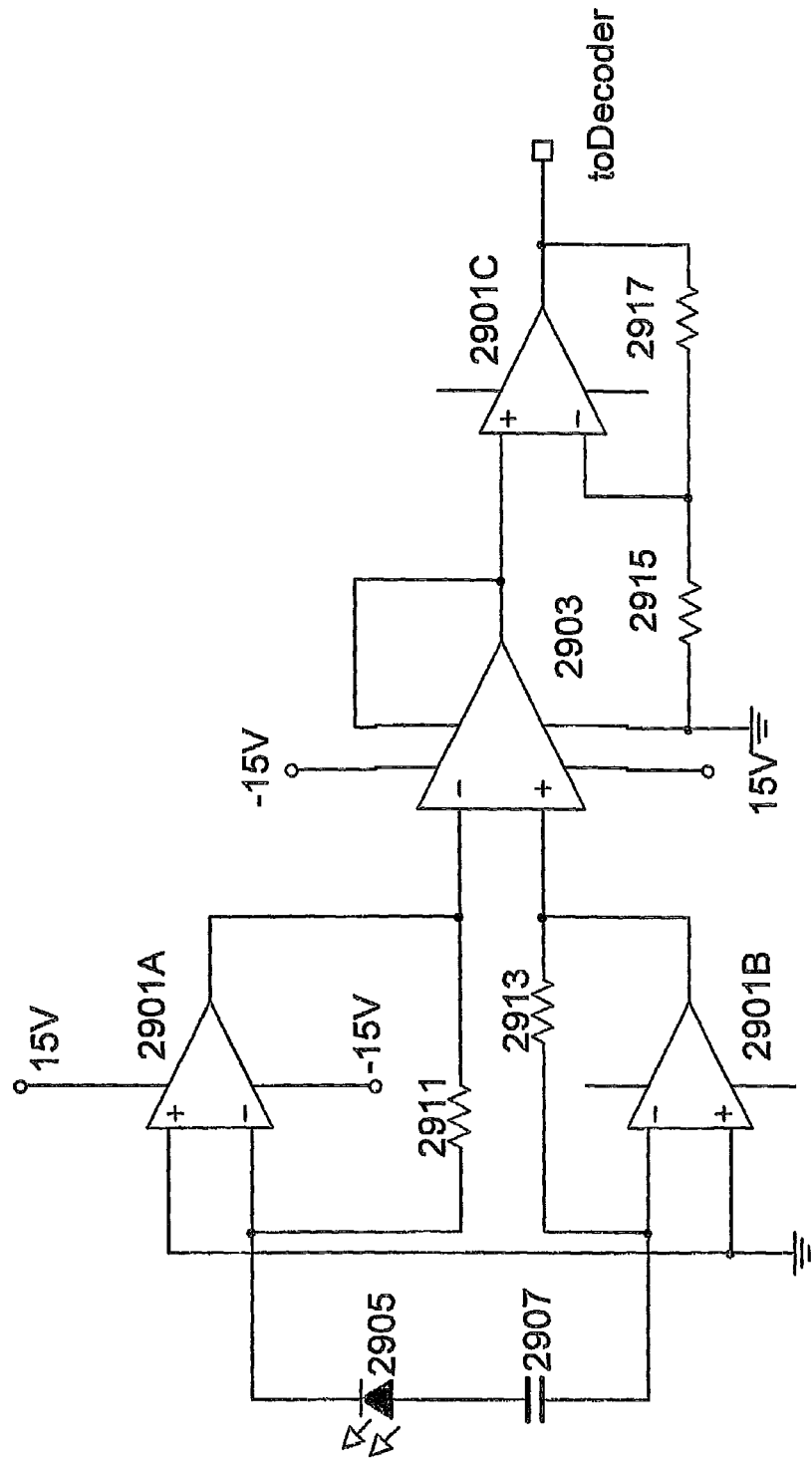
FIG. 23 is an electronic schematic diagram of the prototype optical receiver. The photodiode can be mounted remotely since the intrinsic common mode rejection of the instrumentation amplifier will cancel strong electromagnetic interference. The novelty of this system is that it can be operated in a brightly lit room or even in direct sunlight.

FIG. 23 shows the optical receiver used in this alternative embodiment based on an IR photodetector 2905 and an instrumentation amplifier consisting of op amps 2901A-B and 2903 with discrete components 2911 and 2913 in an unconventional configuration. Ordinarily the photodiode 2905 would be connected as a current source to a single-ended transimpedance amplifier with very high gain. In the novel circuit of the present application a capacitor 2907 is placed in series with the photodiode 2905. The operation of the circuit can be understood easily if one considers the series diode 2905 and capacitor 2907 as a "gain-setting resistor" in an ordinary amplifier. At low frequencies and DC the capacitor 2907 acts as an open circuit, making the gain unity. At high frequencies the diode-capacitor 2905, 2907 combination acts as a resistor which sets the amplifier gain. The net effect is to allow a high gain for short light pulses and no gain for background or ambient illumination. Thus the receiver can be operated in a brightly lit room or even in direct sunlight.

Figure 24:
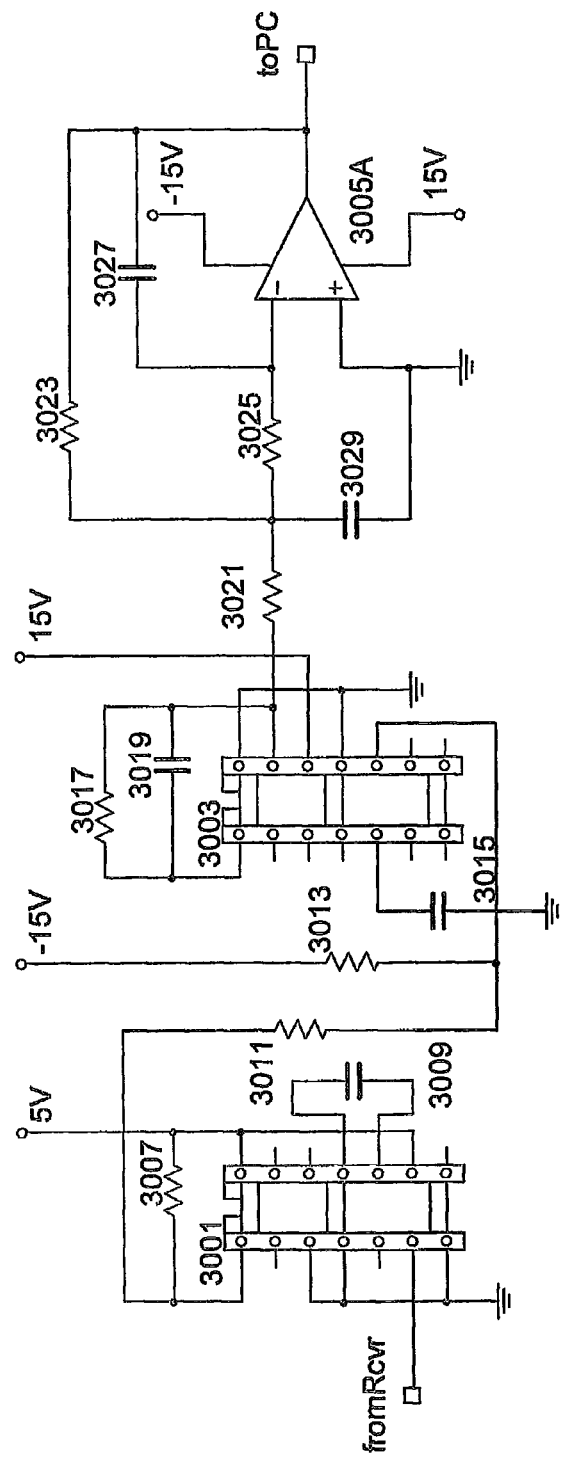
FIG. 24 is a schematic diagram of the prototype IR receiver decoder.

Following an additional gain stage consisting of op amp 2901C and gain setting resistors 2915 and 2917 photodetector output pulses are led to a Schmitt trigger consisting of 74HC121 3001 and timing circuitry 3007 and 3009 and one-shot 3003. This converts the variable amplitude light pulses to a standard amplitude and duration (4.8V, 1.0 µSec). In the final stage shown in FIG. 24 the variable frequency pulse trains are converted back to an analog voltage which varies precisely as the input signal ECG. This is accomplished by a single chip (VFC320) 3003, and support circuitry consisting of RC's 3011, 3013, 3015, 3017 and 3019, which is a voltage-to-frequency (V-F) converter operated in a kind of reverse mode. The converter output is filtered by a multi-pole Bessel low-pass filter, shown as an OPA4277 3005A and discrete RC components 3021, 3023, 3025, 3027, 3029, with cutoff in the range of 35 to 200 Hz to remove any residual high frequency spiking. At this point the ECG is fully recovered and can be processed and displayed as needed.

While the invention has been described with reference to specific embodiments, modifications and variations of the invention may be constructed without departing from the scope of the invention.

We claim:

1. A method for triggering a magnetic resonance imaging system, comprising:

capturing a noisy electrical signal, via at least one main lead, including a biologically generated electrical signal that causes movement in a moving body part of a living being, and noise;

capturing, via at least one magnetic resonance noise lead, a noise reference signal indicative of magnetic resonance electromagnetic noise ambient to the at least one main lead;

receiving, by a receiving device, the captured noisy electrical signal and the noise reference signal;

canceling, by a processing device, the noise reference signal from the captured electrical signal to obtain a processed electrical signal indicative of the biologically generated electrical signal that causes movement in the moving body part of the living being using an adaptive canceling noise filter;

detecting, by a processing device, a characteristic of the processed electrical signal indicative of the biologically generated electrical signal that causes movement in the moving body part of the living being to obtain a trigger signal; and transmitting, by a transmitting device, the trigger signal to cause the magnetic resonance imaging system to capture at least one image including the moving body part of a living being.

2. The method of claim 1, wherein the moving body part is at least one of a heart, blood vessel, and cardiovascular system.

3. The method of claim 1, wherein the moving body part is a heart of a human subject and the at least one main lead is located on the chest of the human subject.

4. The method of claim 1, wherein the moving body part is a heart of a human subject and the at least one magnetic resonance noise lead is located on at least one of an arm or a leg of the human subject.

5. The method of claim 1, wherein the at least one main lead and the at least one magnetic resonance noise lead include carbon filament wires without metallic inclusions.

6. The method of claim 1, wherein the adaptive canceling noise filter is at least one of: a least mean square filter, a recursive least square filter, and a least square lattice filter.

7. The method of claim 1, further comprising:
identifying, by the processing device, a vector statistic based on the processed electrical signal using a Gram-Schmidt Orthogonalization algorithm, wherein the trigger signal transmitted to the magnetic resonance imaging system is the identified vector statistic.

8. A system for triggering a magnetic resonance imaging system, comprising:
at least one main lead configured to capture a noisy electrical signal including a biologically generated electrical signal that causes movement in a moving body part of a living being, and noise;
at least one magnetic resonance noise lead configured to capture a noise reference signal indicative of magnetic resonance gradient electromagnetic noise ambient to the at least one main lead;
a receiving device configured to receive the captured noisy electrical signal and the noise reference signal;
a processing device configured to cancel the noise reference signal from the captured noisy electrical signal to obtain a processed electrical signal indicative of the electrical signal that causes movement in the moving body part of the living being using an adaptive canceling noise filter and configured to detect a characteristic of the processed electrical signal to obtain a trigger signal; and
a transmitting device configured to transmit the trigger signal to a magnetic resonance imaging system to cause the magnetic resonance imaging system to capture at least one image including the moving body part of the living body.

9. The system of claim 8, wherein the moving body part of a living being is at least one of a heart, blood vessel, and cardiovascular system.

10. The system of claim 8, wherein the moving body part of a living being is a heart of a human subject and the at least one main lead is adapted to be located on the chest of the human subject.

11. The system of claim 8, wherein the moving body part of a living being is a heart of a human subject and the at least one magnetic resonance noise lead is adapted to be located on at least one of an arm or a leg of the human subject.

12. The system of claim 8, wherein the at least one main lead and the at least one magnetic resonance noise lead include carbon filament wires without metallic inclusions.

13. The system of claim 8, wherein the adaptive canceling noise filter is at least one of: a least mean square filter, a recursive least square filter, and a least square lattice filter.

14. The system of claim 8, wherein
the processing device is further configured to identify a vector statistic based on the processed electrical signal using a Gram-Schmidt Orthogonalization algorithm, wherein the trigger signal transmitted to the magnetic resonance imaging system is the identified vector statistic.

* * * * *

UNITED STATES PATENT AND TRADEMARK OFFICE
CERTIFICATE OF CORRECTION

| | | |
|---|---|---|
| PATENT NO. | : 8,626,266 B1 | Page 1 of 1 |
| APPLICATION NO. | : 13/315234 | |
| DATED | : January 7, 2014 | |
| INVENTOR(S) | : Thomas H. Frank et al. | |

It is certified that error appears in the above-identified patent and that said Letters Patent is hereby corrected as shown below:

Title Page, Item (73) Assignee: change "Crofton, MA (US)" to -- Crofton, MD (US) --.

Signed and Sealed this
Fifteenth Day of April, 2014

Michelle K. Lee
*Deputy Director of the United States Patent and Trademark Office*